(12) United States Patent
Axt et al.

(10) Patent No.: US 6,355,637 B1
(45) Date of Patent: Mar. 12, 2002

(54) LOCAL ANESTHETIC COMPOUNDS

(75) Inventors: Sabine M. Axt, Sunnyvale; Timothy J. Church, San Mateo; John R. Jacobsen, San Francisco; Thomas E. Jenkins, La Honda; Yu-Hua Ji, Redwood City; Huiwei Wu, Foster City, all of CA (US)

(73) Assignee: Advanced Medicine, Inc., South San Francisco, CA (US)

( * ) Notice: Subject to any disclaimer, the term of this patent is extended or adjusted under 35 U.S.C. 154(b) by 0 days.

(21) Appl. No.: 09/671,626

(22) Filed: Sep. 28, 2000

Related U.S. Application Data

(60) Provisional application No. 60/157,368, filed on Oct. 1, 1999.

(51) Int. Cl.[7] .................... C07D 413/06; C07D 273/08; A61K 31/517
(52) U.S. Cl. ...................... 514/234.5; 514/626; 540/467
(58) Field of Search ...................... 540/467; 514/234.5, 514/626

(56) References Cited

U.S. PATENT DOCUMENTS

| | | | |
|---|---|---|---|
| 3,984,555 A | 10/1976 | Amschler et al. | 424/251 |
| 4,597,903 A | 7/1986 | Gokel et al. | 260/330.6 |
| 5,134,232 A | 7/1992 | Tsien et al. | 540/467 |
| 5,389,630 A | 2/1995 | Sato et al. | 514/218 |
| 5,405,975 A | 4/1995 | Kuhn et al. | 549/347 |
| 5,948,906 A | 9/1999 | Tsien et al. | 540/467 |

OTHER PUBLICATIONS

Ager, I.R., et al. "Synthesis and Central Nervous System Activity of Quinazolones Related to 2–Methyl–3–(o–tolyl)–4(3H)–quinazoline (Methaqualone)." *J. Med. Chem.* 20(3): 379–386 (1977).

Debnath, A.K., et al. "Structure–Based Identification of Small Molecule Antiviral Compounds Targeted to the gp41 Core Structure of the Human Immunodeficiency Virus Type I." *J. Med. Chem.* 42: 3203–3209 (1999).

Gatto, et al. "Synthesis and Binding Properties of Bibracchial Lariat Ethers (BiBBLEs): Surveys of Synthetic Methods and Cation Selectivities." *J. Org. Chem.* 51: 5373–5384 (1986).

Gupta, C.M., et al. "Drugs Acting on the Central Nervous System. Syntheses of Substituted Quinazolones and Quinazolines and Triazepino–and Traizocinoquinazolones." *J. Med. Chem.* 11(2): 392–395 (1968).

Hollowood, J., et al. "Local Anesthetics with Enhanced Affinity for Proteins." *J. Med. Chem.* 10(5): 863–867 (1967).

Kuzma, P.J., et al. "Progress in the Development of Ultra–Long–Acting Local Anesthetics." *Regionals Anesthesia.* 22(6): 543–551 (1997).

Padia, J.K., et al. "Design and Synthesis of Novel Nonpeptide CCK–B Receptor Antagonists." *Bioorg. & Med. Chem. Letts.* 7(7): 805–810 (1997).

Vogtle, F., et al. "Kronenether mit haptophoren bzw. pharmakophoren Gruppen." *Chem. Ber.* 111: 1434–1439 (1978). (summary in English).

Yamashita, T., et al. "Synthesis of Crown Ether Dyes." *Bull. Chem. Soc. Jpn.* 53: 1550–1554 (1980).

Database Chemcats Online! Chemical Abstracts, Columbus, Ohio, US. AN 2000: 927662, Aug. 23, 1999.

*Primary Examiner*—Bruck Kifle
(74) *Attorney, Agent, or Firm*—David E. Boone; Jeffrey A. Hagenah

(57) ABSTRACT

This invention provides novel quinazolinone compounds and pharmaceutically acceptable salts thereof, which are useful as local anesthetics. This invention also provides pharmaceutical compositions containing such compounds; methods for producing local anesthesia in a mammal using such compounds; and processes and intermediates useful for preparing such compounds.

25 Claims, 5 Drawing Sheets

US 6,355,637 B1

LOCAL ANESTHETIC COMPOUNDS

CROSS-REFERENCE TO RELATED APPLICATIONS

This application claims the benefit of U.S. Provisional Application No. 60/157,368, filed on Oct. 1, 1999; the disclosure of which is incorporated herein by reference in its entirety.

BACKGROUND OF THE INVENTION

1. Field of the Invention

This invention is directed to novel quinazolinone compounds which are useful as local anesthetics. This invention is also directed to pharmaceutical compositions comprising such compounds; methods of using such compounds as, for example, local anesthetics; and processes and intermediates for preparing such compounds.

2. State of the Art

Local anesthetics are widely used for preventing and treating various types of pain. However, currently available local anesthetics have a relatively short duration of action and must be repeatedly or continuously administered to provide prolonged pain relief. As a result, such agents are generally unsatisfactory for treating post-surgical or chronic pain. See, for example, Paul J. Kuzma et al., "Progress in the Development of Ultra-Long-Acting Local Anesthetics" *Regional Anesthesia* 1997, 22(6), 543–551. Accordingly, a significant need exists for long-acting local anesthetics to provide effective post-operative analgesia and treatment for chronic pain.

SUMMARY OF THE INVENTION

The present invention provides novel quinazolinone compounds which are useful as local anesthetics. Among other properties, compounds of this invention have been found to provide a longer duration of analgesia compared to currently available local anesthetics.

Accordingly, in one of its composition aspects, this invention provides a compound of formula I:

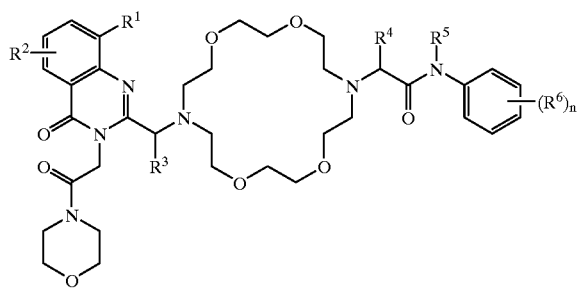

I wherein $R^1$ is selected from the group consisting of hydrogen, $C_{1-6}$ alkyl and $C_{1-6}$ alkoxy;

$R^2$ is selected from the group consisting of hydrogen, $C_{1-6}$ alkyl and $C_{1-6}$ alkoxy;

$R^3$ is hydrogen or $C_{1-6}$ alkyl;

$R^4$ is hydrogen or $C_{1-6}$ alkyl;

$R^5$ is hydrogen or $C_{1-6}$ alkyl;

each $R^6$ is independently selected from the group consisting of $C_{1-6}$ alkyl and $C_{1-6}$ alkoxy;

n is an integer from 0 to 3;

and pharmaceutically acceptable salts and stereoisomers thereof.

This invention is also directed to intermediates useful for preparing compounds of formula I. Accordingly, in another of its composition aspects, this invention provides a compound of formula II:

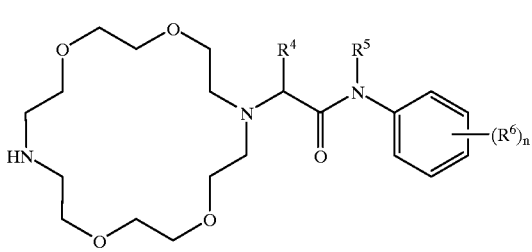

II wherein $R^4$, $R^5$, $R^6$ and n are as defined herein, or a salt thereof, which compounds are useful as intermediates for preparing compounds of formula I.

Additionally, in still another of its composition aspects, this invention provides a compound of formula III:

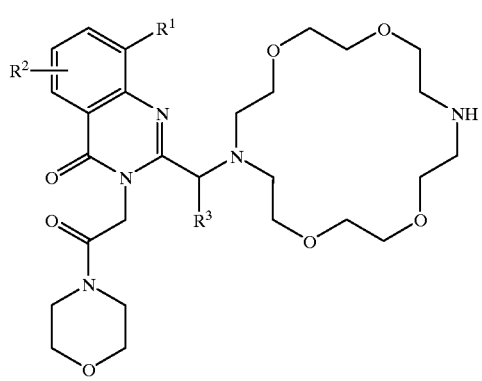

III wherein $R^1$, $R^2$ and $R^3$ are as defined herein, or a salt thereof, which compounds are also useful as intermediates for preparing compounds of formula I.

In yet another of its composition aspects, this invention provides a pharmaceutical composition comprising a pharmaceutically acceptable carrier and a therapeutically effective amount of a compound of formula I, or a pharmaceutically acceptable salt thereof.

The compounds of formula I have been discovered to inhibit or modulate voltage-gated sodium channels associated with nerve conduction. Additionally, the compounds of this invention produce local anesthesia or analgesia when administered to a mammal. Therefore, among other properties, the compounds of formula I are useful as local anesthetics.

Accordingly, in one of its method aspects, this invention is directed to a method for producing local anesthesia or analgesia in a mammal, the method comprising administering to a mammal a pharmaceutical composition comprising a pharamaceutically acceptable carrier and a therapeutically effective amount of a compound of formula I, or a pharmaceutically acceptable salt thereof.

Additionally, in another of its method aspects, this invention provides a method for treating a disease or medical condition associated with or modulated by a volatge-gated sodium channel, the method comprising administering to a patient in need of treatment a pharmaceutical composition comprising a pharamaceutically acceptable carrier and a therapeutically effective amount of a compound of formula I, or a pharmaceutically acceptable salt thereof.

This invention is also directed to processes for preparing compounds of formula I. Accordingly, in another of its method aspects, this invention is directed to a process for preparing a compound of formula I, the process comprising contacting a compound of formula II above with a compound of formula IV:

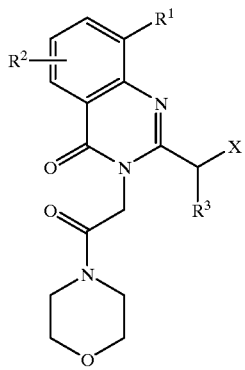

IV wherein $R^1$, $R^2$ and $R^3$ are as defined herein; and X is a leaving group; to provide a compound of formula I. Additionally, in another of its composition aspects, this invention is directed to a compound of formula I prepared by this process.

In still another of its method aspects, this invention is directed to another process for preparing a compound of formula I, the process comprising contacting a compound of formula III with a compound of formula V:

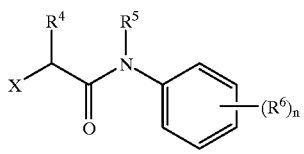

V wherein $R^4$, $R^5$, $R^6$ and n are as defined herein, and X is a leaving group; to provide a compound of formula I. This invention is also directed to a compound of formula I prepared by this process.

In yet another of its method aspects, this invention is directed to the use of a compound of formula I for the manufacture of a medicament. Preferably, the medicament is used to produce local anesthesia or analgesia in a mammal.

DETAILED DESCRIPTION OF THE INVENTION

Figure 1A:
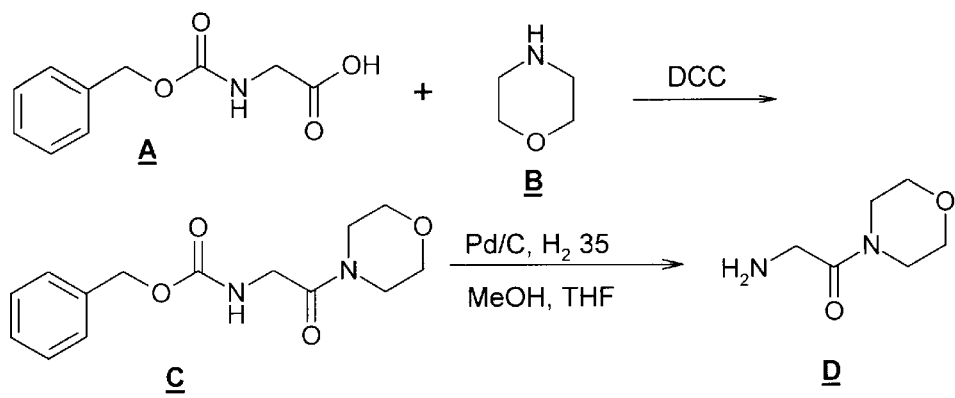
FIGS. 1A–1C illustrate the synthesis of a representative compound of this invention using an intermediate of formula II.

This invention relates to novel quinazolinone compounds having formula I. In the presence of water, such quinazolinone compounds exist in equilibrium with the corresponding diamide as shown below:

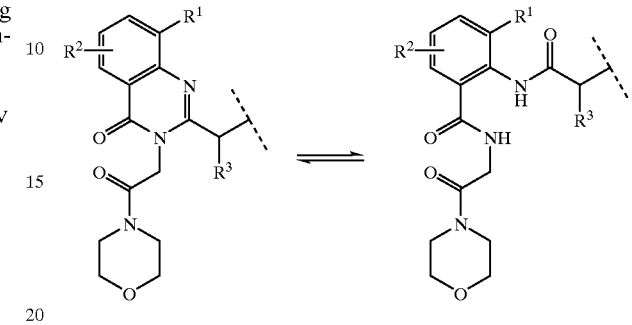

and such diamide compounds are included within the scope of this invention.

When unprotonated, the compounds of formula I can also form complexes with various cations, such as sodium ions. Such complexes are also included within the scope of this invention.

Additionally, in some cases, the quinazolinone compounds of this invention will contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) are included within the scope of this invention. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Preferred Embodiments

In the compounds of formula I, the following substituents and values are preferred.

$R^1$ is preferably hydrogen or $C_{1-6}$ alkyl. More preferably, $R^1$ is $C_{1-4}$ alkyl. Preferred $R^1$ groups include methyl, ethyl and n-propyl. An especially preferred $R^1$ group is methyl.

$R^2$ is preferably hydrogen.

Preferably, $R^3$ is hydrogen or $C_{1-4}$ alkyl. More preferably, $R^3$ is hydrogen, methyl or ethyl. Still more preferably, $R^3$ is hydrogen.

Preferably, $R^4$ is hydrogen or $C_{1-4}$ alkyl. More preferably, $R^4$ is hydrogen, methyl, ethyl or n-propyl. In one preferred embodiment, $R^4$ is methyl or ethyl and the carbon to which $R^4$ is attached is the (S)-stereoisomer. In another preferred embodiment, $R^4$ is methyl or ethyl and the carbon to which $R^4$ is attached is the (R)-stereoisomer.

$R^5$ is preferably hydrogen or $C_{1-4}$ alkyl. More preferably, $R^5$ is hydrogen, methyl or ethyl. Still more preferably, $R^5$ is hydrogen.

Preferably, each $R^6$ is independently $C_{1-6}$ alkyl. More preferably, each $R^6$ is independently $C_{1-4}$ alkyl. Preferred $R^6$ groups include methyl, ethyl, n-propyl, isopropyl and tert-butyl. An especially preferred $R^6$ group is methyl. In preferred embodiments, each $R^6$, and the phenyl ring to which they are attached, form a 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6,-trimethylphenyl, 2,4,5-trimethylphenyl, 2,4,6-trimethylphenyl, 3,4,5-trimethylphenyl, 2-ethylphenyl, 2-ethyl-6-methylphenyl or 2-isopropylphenyl group. In especially preferred embodiments, each $R^6$ and the phenyl ring to which they are attached form a 2-methylphenyl or 2,6-dimethylphenyl group.

Preferably, n is an integer from 1 to 3; more preferably, n is 1 or 2.

In one of its preferred embodiments, this invention is directed to a compound of formula I wherein $R^1$ is $C_{1-4}$ alkyl; $R^2$, $R^3$ and $R^1$ are hydrogen; $R^4$ is hydrogen or $C_{1-4}$ alkyl; $R^6$ is $C_{1-4}$ alkyl; and n is an integer from 1 to 3.

In another of its preferred embodiments, this invention is directed to a compound of formula I wherein $R^1$ is methyl; $R^2$, $R^3$ and $R^5$ are hydrogen; $R^4$ is hydrogen, methyl or ethyl; $R^6$ is methyl; and n is an integer from 1 to 3.

Particularly preferred compounds of formula I include those having the formula shown in Table I, and pharmaceutically acceptable salts thereof.

The compounds in Table I are racemic unless otherwise indicated.

Accordingly, this invention is also directed to each of the following compounds:

7-[(8-methyl-3-(morpholin-4-ylcarbonylmethyl)-4(3H)-quinazolinon-2-yl)methyl]-16-[(R)-(2-methylphenylaminocarbonyl)prop-1-yl]-1,4,10,13-tetraoxa-7,16-diazacyclooctadecane (Compound 1);

7-[(8-methyl-3-(morpholin-4-ylcarbonylmethyl)-4(3H)-quinazolinon-2-yl)methyl]-16-[(S)-(2-methylphenylaminocarbonyl)prop-1-yl]-1,4,10,13-tetraoxa-7,16-diazacyclooctadecane (Compound 2);

7-[(8-methyl-3-(morpholin-4-ylcarbonylmethyl)-4(3H)-quinazolinon-2-yl)methyl]-16-[(2-methylphenylaminocarbonyl)prop-1-yl]-1,4,10,13-tetraoxa-7,16-diazacyclooctadecane (Compound 3);

7-[(8-methyl-3-(morpholin-4-ylcarbonylmethyl)-4(3H)-quinazolinon-2-yl)methyl]-16-[(2,4,6-trimethylphenylaminocarbonyl)methyl]-1,4,10,13-tetraoxa-7,16-diazacyclooctadecane (Compound 4);

7-[(8-methyl-3-(morpholin-4-ylcarbonylmethyl)-4(3H)-quinazolinon-2-yl)methyl]-16-[1-(2-methylphenylaminocarbonyl)ethyl]-1,4,10,13-tetraoxa-7,16-diazacyclooctadecane (Compound 5);

TABLE I

| No. | $R^1$ | $R^3$ | $R^4$ | $R^{6a}$ | $R^{6b}$ | $R^{6c}$ | $R^{6d}$ | $R^{6e}$ |
|---|---|---|---|---|---|---|---|---|
| 1 | —$CH_3$ | —H | —$CH_2CH_3$ R-isomer | —$CH_3$ | —H | —H | —H | —H |
| 2 | —$CH_3$ | —H | —$CH_2CH_3$ S-isomer | —$CH_3$ | —H | —H | —H | —H |
| 3 | —$CH_3$ | —H | —$CH_2CH_3$ | —$CH_3$ | —H | —H | —H | —H |
| 4 | —$CH_3$ | —H | —H | —$CH_3$ | —H | —$CH_3$ | —H | —$CH_3$ |
| 5 | —$CH_3$ | —H | —$CH_3$ | —$CH_3$ | —H | —H | —H | —H |
| 6 | —$CH_3$ | —H | —$CH_2CH_3$ | —$CH_3$ | —H | —H | —H | —$CH_3$ |
| 7 | —$CH_3$ | —H | —$CH_2CH_3$ | —$CH_2CH_3$ | —H | —H | —H | —H |
| 8 | —$CH_3$ | —H | —$(CH_2)_2CH_3$ | —$CH_3$ | —H | —H | —H | —H |
| 9 | —$CH_3$ | —H | —H | —$CH_3$ | —H | —H | —H | —$CH_3$ |
| 10 | —$CH_3$ | —H | —H | —$CH(CH_3)_2$ | —H | —H | —H | —H |
| 11 | —$CH_3$ | —H | —H | —$CH_2CH_3$ | —H | —H | —H | —H |
| 12 | —$CH_3$ | —H | —H | —$CH_3$ | —H | —H | —H | —H |
| 13 | —$CH_3$ | —H | —H | —$CH_2CH_3$ | —H | —H | —H | —$CH_3$ |
| 14 | —$CH_3$ | —$CH_2CH_3$ | —$CH_2CH_3$ | —$CH_3$ | —H | —H | —H | —H |
| 15 | —$CH_3$ | —H | —H | —$CH_3$ | —$CH_3$ | —H | —H | —H |
| 16 | —$CH_3$ | —H | —H | —$CH_3$ | —H | —$CH_3$ | —H | —H |
| 17 | —$CH_3$ | —H | —H | —$CH_3$ | —H | —H | —$CH_3$ | —H |
| 18 | —$CH_3$ | —H | —H | —H | —$CH_3$ | —$CH_3$ | —H | —H |
| 19 | —$CH_3$ | —H | —H | —H | —$CH_3$ | —H | —$CH_3$ | —H |
| 20 | —H | —H | —$CH_2CH_3$ | —$CH_3$ | —H | —H | —H | —H |

7-[(8-methyl-3-(morpholin-4-ylcarbonylmethyl)-4(3H)-quinazolinon-2-yl)methyl]-16-[(2,6-dimethylphenylaminocarbonyl)prop-1-yl]-1,4,10,13-tetraoxa-7,16-diazacyclooctadecane (Compound 6);

7-[(8-methyl-3-(morpholin-4-ylcarbonylmethyl)-4(3H)-quinazolinon-2-yl)methyl]-16-[(2-ethylphenylaminocarbonyl)prop-1-yl]-1,4,10,13-tetraoxa-7,16-diazacyclooctadecane (Compound 7);

7-[(8-methyl-3-(morpholin-4-ylcarbonylmethyl)-4(3H)-quinazolinon-2-yl)methyl]-16-[(2-methylphenylaminocarbonyl)but-1-yl]-1,4,10,13-tetraoxa-7,16-diazacyclooctadecane (Compound 8);

7-[(8-methyl-3-(morpholin-4-ylcarbonylmethyl)-4(3H)-quinazolinon-2-yl)methyl]-16-[(2,6-dimethylphenylaminocarbonyl)methyl]-1,4,10,13-tetraoxa-7,16-diazacyclooctadecane (Compound 9);

7-[(8-methyl-3-(morpholin-4-ylcarbonylmethyl)-4(3H)-quinazolinon-2-yl)methyl]-16-[(2-isopropylphenylaminocarbonyl)methyl]-1,4,10,13-tetraoxa-7,16-diazacyclooctadecane (Compound 10);

7-[(8-methyl-3-(morpholin-4-ylcarbonylmethyl)-4(3H)-quinazolinon-2-yl)methyl]-16-[(2-ethylphenylaminocarbonyl)methyl]-1,4,10,13-tetraoxa-7,16-diazacyclooctadecane (Compound 11);

7-[(8-methyl-3-(morpholin-4-ylcarbonylmethyl)-4(3H)-quinazolinon-2-yl)methyl]-16-[(2-methylphenylaminocarbonyl)methyl]-1,4,10,13-tetraoxa-7,16-diazacyclooctadecane (Compound 12);

7-[(8-methyl-3-(morpholin-4-ylcarbonylmethyl)-4(3H)-quinazolinon-2-yl)methyl]-16-[(2-ethyl-6-methylphenylaminocarbonyl)methyl]-1,4,10,13-tetraoxa-7,16-diazacyclooctadecane (Compound 13);

7-[(8-methyl-3-(morpholin-4-ylcarbonylmethyl)-4(3H)-quinazolinon-2-yl)prop-1-yl]-16-[(2-methylphenylaminocarbonyl)prop-1-yl]-1,4,10,13-tetraoxa-7,16-diazacyclooctadecane (Compound 14);

7-[(8-methyl-3-(morpholin-4-ylcarbonylmethyl)-4(3H)-quinazolinon-2-yl)methyl]-16-[(2,3-dimethylphenylaminocarbonyl)methyl]-1,4,10,13-tetraoxa-7,16-diazacyclooctadecane (Compound 15);

7-[(8-methyl-3-(morpholin-4-ylcarbonylmethyl)-4(3H)-quinazolinon-2-yl)methyl]-16-[(2,4-dimethylphenylaminocarbonyl)methyl]-1,4,10,13-tetraoxa-7,16-diazacyclooctadecane (Compound 16);

7-[(8-methyl-3-(morpholin-4-ylcarbonylmethyl)-4(3H)-quinazolinon- 2-yl)methyl]-16-[(2,5-dimethylphenylaminocarbonyl)methyl]-1,4,10,13-tetraoxa-7,16-diazacyclooctadecane (Compound 17);

7-[(8-methyl-3-(morpholin-4-ylcarbonylmethyl)-4(3H)-quinazolinon-2-yl)methyl]-16-[(3,4-dimethylphenylaminocarbonyl)methyl]-1,4,10,13-tetraoxa-7,16-diazacyclooctadecane (Compound 18);

7-[(8-methyl-3-(morpholin-4-ylcarbonylmethyl)-4(3H)-quinazolinon-2-yl)methyl]-16-[(3,5-dimethylphenylaminocarbonyl)methyl]-1,4,10,13-tetraoxa-7,16-diazacyclooctadecane (Compound 19);

7-[(3-(morpholin-4-ylcarbonylmethyl)-4(3H)-quinazolinon-2-yl)methyl]-16-[(2-methylphenylaminocarbonyl)methyl]-1,4,10,13-tetraoxa-7,16-diazacyclooctadecane (Compound 20);

and pharmaceutically acceptable salts and stereoisomers thereof. In particular, the (R) and (S) isomers of Compounds 5, 6, 7, 8 and 20; and the (R,R), (R,S), (S,R) and (S,S) isomers of Compound 14 are specifically included herein.

Definitions

When describing the compounds, compositions, methods and processes of this invention, the following terms have the following meanings, unless otherwise indicated.

The term "alkyl" refers to a monovalent saturated hydrocarbon group which may be linear or branched or combinations thereof. Such alkyl groups preferably contain from 1 to 10 carbon atoms; more preferably, from 1 to 6 carbon atoms; and still more preferably, from 1 to 4 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkoxy" refers to a group of the formula —OR, where R is an alkyl group as defined herein. Representative alkoxy groups include, by way of example, methoxy, ethoxy, n-propoxy, isopropoxy, n-butoxy, sec-butoxy, isobutoxy, tert-butoxy, n-pentoxy, n-hexoxy and the like.

The term "pharmaceutically acceptable salt" refers to a salt prepared from a base or acid which is acceptable for administration to a patient, such as a mammal. Such salts can be derived from pharmaceutically acceptable inorganic or organic bases and from pharmaceutically acceptable inorganic or organic acids. Salts derived from pharmaceutically acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuiric, tartaric, p-toluenesulfonic and the like. Particularly preferred are citric, hydrobromic, hydrochloric, maleic, phosphoric, sulfuric and tartaric acids.

The term "therapeutically effective amount" refers to an amount sufficient to effect treatment when administered to a patient in need of treatment.

The term "treatment" as used herein refers to the treatment of a disease or medical condition (i.e., pain) in a patient, such as a mammal (particularly a human or a companion animal) which includes:

(a) preventing the disease or medical condition from occurring, i.e., prophylactic treatment of a patient;

(b) ameliorating the disease or medical condition, i.e., eliminating or causing regression of the disease or medical condition in a patient;

(c) suppressing the disease or medical condition, i.e., slowing or arresting the development of the disease or medical condition in a patient; or (d) alleviating the symptoms of the disease or medical condition in a patient.

The term "steroisomer" refers to an enantiomer, diastereomer or diasteromeric mixture of a compound containing one or more asymmetric center(s). For compounds having one or more asymmetric center(s), the present invention includes individual steroisomers (i.e., the R or S isomers for compounds containing one chiral center and the R,R, RS, SR and SS isomers for compounds containing two chiral centers), enriched steroisomeric mixtures and racemic mixtures of such compounds.

The term "leaving group" refers to a functional group which can be displaced by a nucleophilic functional group in a nucleophilic substitution reaction. By way of example, representative leaving groups include chloro, bromo and iodo groups; and sulfonic ester groups, such as mesylate, tosylate, brosylate, nosylate and the like.

The phrase "disease or medical condition associated with or modulated by a voltage-gated sodium channel" refers to all disease states or medical conditions that are associated with (e.g., caused by) the activity of a voltage-gated sodium channel or which are modulated by a voltage-gated sodium channel, which disease or medical condition can be treated with an agent that modulates the activity of such sodium channels.

General Synthetic Procedures

The quinazolinone compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be readily determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Third Edition, Wiley, New York, 1999, and references cited therein.

In a preferred method of synthesis, the compounds of formula I are prepared by reacting an intermediate of formula II:

II

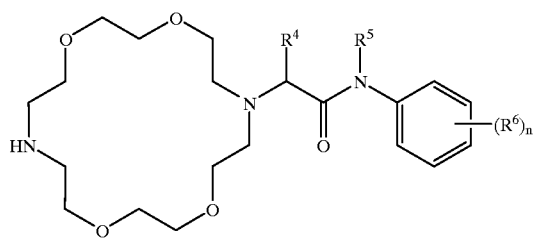

wherein $R^4$, $R^5$, $R^6$ and n are as defined herein, with a quinazolinone derivative of formula IV:

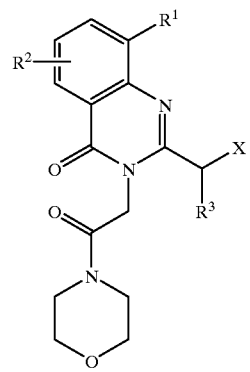

IV wherein $R^1$, $R^2$ and $R^3$ are as defined herein; and X is a leaving group; to provide a compound of formula I.

Typically, this reaction is conducted by contacting a compound of formula II with about 1.0 to about 1.2 equivalents, preferably with about 1.1 equivalents, of quinazolinone IV in an inert diluent, such as acetonitrile, at a temperature ranging from about 25° C. to about 120° C., preferably from 50° C. to 70° C., for about 6 to 24 hours, or until the reaction is substantially complete. Preferably, this reaction is conducted in the presence of an excess, preferably 1.1 to 1.2 equivalents, of a tertiary amine, such as diisopropylethylamine. Upon completion of the reaction, the reaction product, i.e., a compound of formula I, is isolated and optionally purified using conventional procedures, such as column chromatography, recrystallization and the like.

Alternatively, compounds of formula I can be prepared by reacting a compound of formula II with an 2-amidobenzamide compound of formula IVa:

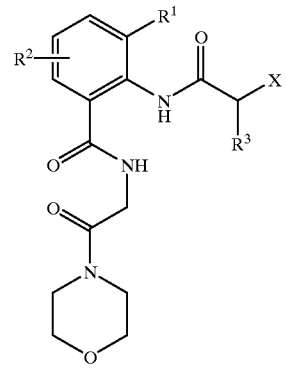

IVa wherein $R^1$, $R^2$ and $R^3$ are as defined herein; and X is a leaving group; to provide a compound of formula I. In this reaction, the quinazolinone ring is typically formed in situ. When $R^3$ is other than hydrogen, the quinazolinone ring may not form under these reaction conditons and, if so, the resulting coupled diamide is heated in acetic acid and ethanol to form the desired quinazolinone ring.

This reaction is typically conducted by contacting a compound of formula II with about 1.0 to about 1.3 equivalents, preferably with about 1.3 equivalents, of the 2-amidobenzamide IVa in an inert diluent, such as ethanol/DMF, at a temperature ranging from about 70° C. to about 130° C., preferably at about 120° C., in a sealed reaction vessel for about 4 to 24 hours, or until the reaction is substantially complete. Preferably, this reaction is conducted in the presence of an excess, preferably 1.1 to 1.5 equivalents, of a base, preferably a tertiary amine, such as diisopropylethylamine. Upon completion of the reaction, the reaction product, i.e., compound of formula I, is isolated and optionally purified using conventional procedures, such as column chromatography, recrystallization and the like.

The compounds of formula II employed in the above reactions can be readily prepared from commercially available starting materials and reagents. By way of illustration, compounds of formula II can be prepared as shown in Scheme I.

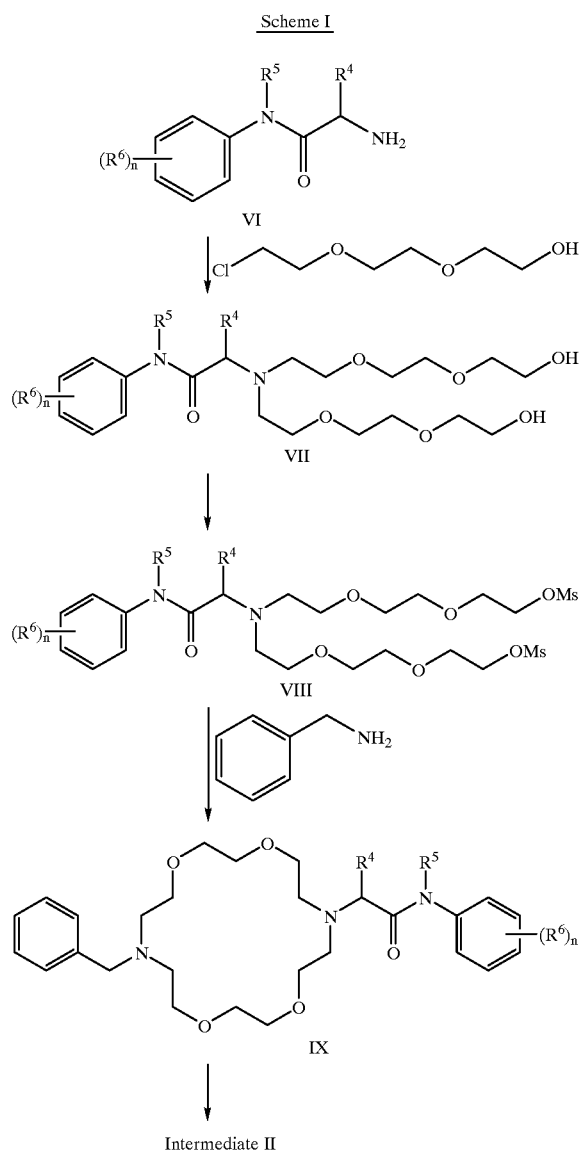

Intermediate II

As shown in Scheme I, α-aminocarboxamide VI is reacted with 2-[2-(chloroethoxy)ethoxy]ethanol to form diol intermediate VII. This reaction is typically conducted by contacting VI with at least two equivalents, preferably 2.2 equivalents, of 2-[2-(chloroethoxy)ethoxy]ethanol in the presence of sodium iodide (preferably about 1 equivalent) and an excess of sodium carbonate (preferably about 3.5 equivalents) at a temperature ranging from about 80° C. to about 150° C., preferably 120° C., for 4 to 24 hours, or until the reaction is substantially complete.

The α-aminocarboxamides of formula VI employed in this reaction are readily prepared from commercially available starting materials and reagents using conventional procedures. For example, such compounds can be prepared by coupling an N-protected α-aminoacid, such as N-Boc-glycine, N-Boc-alanine, N-Boc-2-aminobutyric acid and the like, with an appropriately substituted phenylamine, such as o-toluidine, 2,6-dimethylaniline and the like, using conventional peptide coupling reagents. Suitable peptide coupling reagents include, by way of example, carbodimides, such as 1,3-dicyclohexylcarbodiimide (DCC), 1-(3-dimethylaminopropyl)-3-ethylcarbodiimide (EDC) and the like; or 1-hydroxy-7-azabenzotriazole (HOAT) and N-[(dimethylamino-1H-1,2,3-triazoleo[4,5-b]pyridin-1-ylmethylene]-N-methylmethanaminium hexafluorophosphate N-oxide (HATU). After the coupling reaction, the protecting group is removed using conventional procedures to afford the α-aminocarboxamide of formula VI.

After formation of diol VII, the diol is then converted into the dimesylate VIII using conventional reagents and reaction conditions. By way of example, diol VIII can be reacted with at least two equivalents of methanesulfonyl chloride in the presence of an excess of a tertiary amine, such as diisopropylethylamine, to afford dimesylate VIII. Typically, this reaction is conducted in an inert diluent, such as dichloromethane, at a temperature ranging from about −20° C. to about 0° C. for about 0.5 to 6 hours, or until the reaction is substantially complete. If desired, other sulfonate esters may be employed in this reaction in place of methanesulfonyl chloride, such as p-toluenesulfonyl chloride and the like.

Reaction of dimesylate VIII with benzylamine then affords intermediate IX. Typically, this reaction is conducted by contacting benzylamine with 1.0 to 1.2 equivalents of the dimesylate VIII in the presence of excess sodium iodide (preferably about 2.2 equivalents) and excess sodium carbonate (preferably 3.5 equivalents). This reaction is typically conducted in an inert diluent, such as acetonitrile, at a temperature ranging from about 50° C. to about 100° C. for about 24 to 48 hours, or until the reaction is substantially complete, to afford intermediate IX.

Removal of the benzyl group from intermediate IX by conventional hydrogenolysis then affords intermediate II. Typically, this reaction is conducted by contacting intermediate IX with hydrogen at a pressure ranging from about 20 to about 50 psi in the presence of a catalyst, such as 10% palladium on carbon. This reaction is typically conducted in an inert diluent, such as methanol, at ambient temperature for about 2 to 24 hours, or until substantially complete.

Alternatively, intermediate II can be prepared by interchanging intermediate VI and benzylamine in Scheme I, i.e., benzylamine can be reacted with 2-[2-(chloroethoxy) ethoxy]ethanol and, after subsequent formation of the dimesylate of the resulting diol, intermediate VI can be reacted with the dimesylate to afford intermediate IX. Additionally, 1,2-bis-(2-iodoethoxy)ethane may be used in place of 2-[2-(chloroethoxy)ethoxy]ethanol in the above reactions to form an intermediate diiodo compound which may be used in place of the dimesylate.

In another preferred method of synthesis, the compounds of formula I are prepared by first reacting a mono-N-protected 1,4,10,13-tetraoxa-7,16-diazacyclooctadecane (such as the mono-N-Boc derivative) with a compound of the formula:

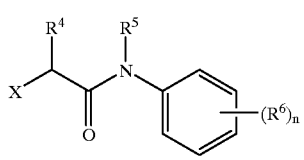

X

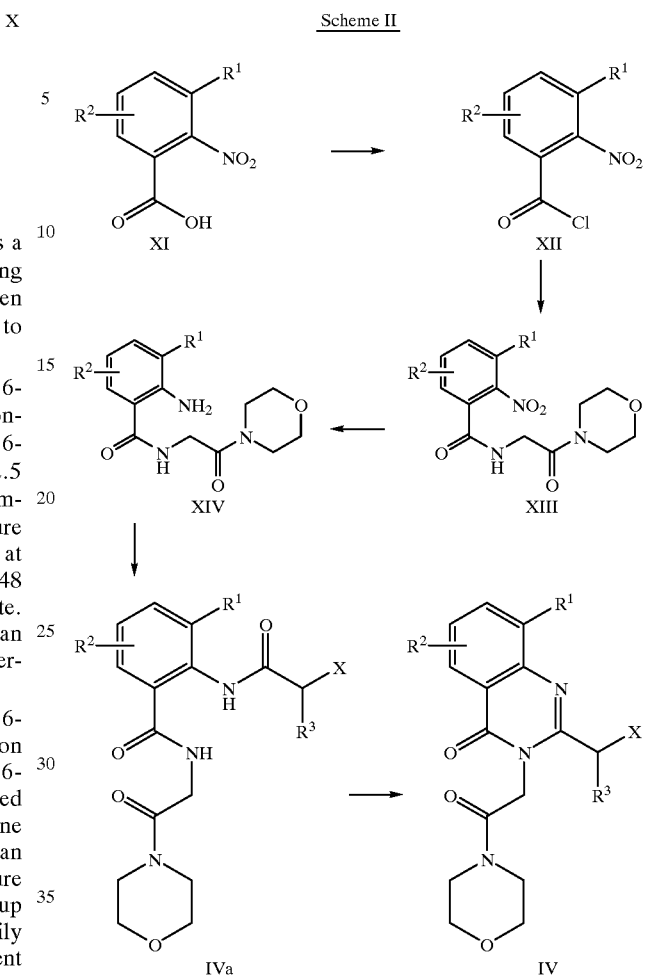

Scheme II wherein $R^4$, $R^5$, $R^6$ and n are as defined herein, and X is a leaving group; to afford, after removal of the Boc protecting group, an intermediate of formula II. Compound II is then reacted with intermediate IV or IVa as described above to provide a compound of formula I.

Reaction of the mono-protected 1,4,10,13-tetraoxa-7,16-diazacyclooctadecane with compound X is typically conducted by contacting the protected 1,4,10,13-tetraoxa-7,16-diazacyclooctadecane with about 1.0 to about 2.5 equivalents, preferably with about 2.0 equivalents, of compound X in an inert diluent, such as ethanol, at a temperature ranging from about 70° C. to about 130° C., preferably at about 120° C., in a sealed reaction vessel for about 6 to 48 hours, or until the reaction is substantially complete. Preferably, this reaction is conducted in the presence of an excess, preferably 1.1 to 2.5 equivalents, of a base, preferably a tertiary amine, such as diisopropylethylamine.

A representative mono-protected 1,4,10,13-tetraoxa-7,16-diazacyclooctadecane suitable for use in the above reaction is N-tert-butoxycarbonyl-(Boc)-1,4,10,13-tetraoxa-7,16-diazacyclooctadecane. This compound is readily prepared by contacting 1,4,10,13-tetraoxa-7,16-diazacyclooctadecane with about one equivalent of di-tert-butyl dicarbonate in an inert diluent, such as 1,4-dioxane, at ambient temperature for about 6 to about 24 hours. When a Boc protecting group is employed in the above reaction, the Boc group is readily removed using conventional procedures, such as treatment with trifluoroacetic acid, after the reaction is complete. Other mono-protected 1,4,10,13-tetraoxa-7,16-diazacyclooctadecane derivatives can also be readily prepared using reagents and procedures well-known in the art.

The compounds of formula X employed in the above reaction can also be readily prepared from commercially available starting materials using procedures and reagents well-known in the art. For example, an appropriately substituted phenylamine, such as o-toluidine, can be readily coupled to an α-halo carboxylic acid halide, such as α-bromobutyryl bromide, α-chloropropionyl chloride, α-chloroacetyl chloride and the like, to form an intermediate of formula X. This reaction is typically conducted by contacting the substituted phenylamine with an excess, preferably 1.1 to 1.3 equivalents, of the α-halo carboxylic acid halide, in an inert diluent, such as glacial acetic acid, at a temperature of about 0° C. for about 1 to 24 hours.

Alternatively, if desired, a mono-N-protected 1,4,10,13-tetraoxa-7,16-diazacyclooctadecane (such as the mono-N-Boc derivative) can first be reacted with a intermediate of formula IV or IVa, to afford, after removal of the protecting group, an intermediate of formula III. This compound can then be reacted a compound of formula X to provide a compound of formula I. These reactions may be conducted using the reaction conditions similar or identical to those described above.

The intermediates of formula IV and IVa employed in the reactions described herein are readily prepared using, for example, the procedures illustrated in Scheme II.

where $R^1$, $R^2$ and $R^3$ are as defined herein, and X is a leaving group.

As shown in Scheme II, a 2-nitrobenzoic acid XI, such as 3-methyl-2-nitrobenzoic acid, is first converted into the corresponding acid chloride XII using conventional reagents and reaction conditions. For example, this reaction can be conducted by contacting XI with excess oxalyl chloride in the presense of a catalytic amount of DMF to afford the acid chloride XII. The acid chloride XII is then reacted with glycine morpholinyl amide (prepared by coupling morpholine to N-carbobenzyloxy(Cbz)-glycine using conventional peptide coupling reagents) to provide compound XIII. Typically, this reaction is conducted by contacting the glycine morpholinyl amide with about 1.1 to about 1.2 equivalents of XII in an inert diluent, such as dichloromethane, in the presence of a trialkylamine, such as diisopropylethylamine. This reaction is typically conducted at about 0° C. for about 0.5 to about 12 hours to afford XIII. The nitro group of XIII is then reduced to the corresponding amine XIV using, for example, hydrogen in the presence of a catalyst, such as palladium on carbon. This reaction is typically conducted at ambient temperature at a pressure of about 25 to 25 psi of hydrogen under the reaction is substantially complete. Alternatively, intermediate XIV can be prepared by reducing the nitro group of compound XI to form the corresponding 2-aminobenzoic acid derivative. This compound can then be coupled to glycine methyl ester using conventional peptide coupling reagents and the resulting methyl ester displaced with morphine at, for example, about 130° C. to afford XIV. The amine XIV is then coupled to, for example, an α-halo carboxylic acid halide, such as α-bromobutyryl bromide, α-chloropropionyl chloride, α-chloroacetyl chloride and the like, to form an intermediate of formula IVa. This reaction is typically conducted by contacting the amine XIV with an excess, preferably 1.1 to 1.3 equivalents, of the α-halo carboxylic acid halide, in an inert diluent, such as glacial acetic acid, at a temperature of about 0° C. for about 1 to 24 hours. Intermediate IVa may be used in the above reactions or, if desired, the quinazolinone ring may be formed by heating IVa in acetic acid and ethanol at a temperature of about 60° C. to about 100° C., preferably at about 85° C., for about 6 to about 24 hours, or until the reaction is substantially complete.

Further details regarding specific reaction conditions and procedures for preparing representative compounds of this invention are described in the Examples set forth below. Additionally, other procedures and examples of preparing compounds of this invention are disclosed in co-pending U.S. patent application Ser. No. 09/671,630, filed on even date herewith, and entitled "Novel Local Anesthetic Compounds", the disclosure of which is incorporated herein by reference in its entirety.

Pharmaceutical Formulations

When employed as pharmaceuticals, the compounds of formula I are typically administered in the form of a pharmaceutical composition. Accordingly, this invention is directed to pharmaceutical compositions which contain one or more of compounds of formula I, or a pharmaceutically acceptable salt thereof, as the active ingredient, and one or more pharmaceutically acceptable excipients, carriers, diluents, permeation enhancers, solubilizers, adjuvants and the like.

The compounds of this invention can also be administered in combination with other therapeutic agents including, by way of illustration, other local anesthetics, such as lidocaine, benzocaine, dyclonine, pramoxine, etidocaine, mepivacaine, chloroprocaine, procaine, bupivacaine, levobupivacaine, ropivacaine and the like; vasoconstrictors, such as epinephrine, phenylephrine, ephedrine, pseudoephedrine and the like; opiates, such as morphine and fentanyl (used to provide epidural/spinal anesthesia); NMDA antagonists, such as dextromethorphan; clonidine; antiinflammatory agents; antibiotics; and the like.

Accordingly, in a preferred embodiment, this invention is directed to a pharmaceutical composition comprising a pharmaceutically acceptable excipient and a therapeutically effective amount of a combination of a local anesthetic, preferably lidocaine, and a compound of formula I, or pharmaceutically acceptable salts thereof. In another preferred embodiment, this invention is directed to a pharmaceutical composition comprising a pharmaceutically acceptable excipient and a therapeutically effective amount of a combination of a vasoconstrictor, preferably epinephrine, and a compound of formula I, or pharmaceutically acceptable salts thereof.

The compounds of this invention may be formulated using conventional techniques such as those described in *Remington's Pharmaceutical Sciences*, Mace Publishing Co., Philadelphia, Pa. 17th Ed. (1985) and "Modern Pharmaceutics," Marcel Dekker, Inc. $3^{rd}$ Ed. (G. S. Banker & C. T. Rhodes, Eds.). Pharmaceutically acceptable salts of the active agents (e.g., acid addition salts) may be prepared using standard procedures known to those skilled in the art of synthetic organic chemistry and described, e.g., by J. March, *Advanced Organic Chemistry: Reactions, Mechanisms and Structure*, $4^{th}$ Ed. (New York: Wiley-Interscience, 1992).

When preparing the pharmaceutical compositions of this invention, the active ingredient is customarily diluted by an excipient. Representative examples of suitable excipients include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include lubricating agents, such as talc, magnesium stearate and mineral oil; wetting agents; emulsifying and suspending agents; preserving agents, such as methyl- and propylhydroxy-benzoates; sweetening agents; and flavoring agents.

Alternatively, the compounds of this invention may be solubilized and encapsulated (e.g., in a liposome or a biodegradable polymer), or used in the form of microcrystals coated with an appropriate nontoxic lipid (see, e.g., P. J. Kuzma et al, *Regional Anesthesia* 22 (6): 543–551 (1997).

The compounds of formula I may be administered by any of the accepted modes of administration for agents having similar utilities, for example, by oral, topical, parenteral (e.g., intradermal, intravenous, subcutaneous, intramuscular), intra-articular, intraspinal, epidural, rectal, vaginal, or transdermal/transmucosal routes. The most suitable route will depend on the nature and severity of the condition being treated and will be determined by a physician. Subcutaneous, intradermal and percutaneous injections (intended to deliver the agent in close proximity to a peripheral nerve trunk) are preferred routes of administration for the compounds of this invention.

By way of example, the pharmaceutical compositions may be formulated as oral sprays. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

For topical use, the pharmaceutical compositions can be in the form of emulsions, creams, jelly, solutions, ointments containing, for example, up to 5% by weight of the active compound.

For parenteral administration, the pharmaceutical compositions can be in the form of sterile injectable solutions and sterile packaged powders. Preferably, injectable solutions are formulated at a pH of 4.5±0.3.

The pharmaceutical compositions of the invention can also be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al, *Regional Anesthesia* 22 (6): 543–551 (1997), all of which are incorporated herein by reference.

Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252; 5,719,197; and 4,992,445, all of which are incorporated herein by reference. Such patches may be constructed for continuous, pulsatile, or on demand delivery of pharmaceutical agents.

The pharmaceutical compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect in association with a suitable pharmaceutical excipient (e.g., provided in an ampoule).

The compounds of this invention are typically administered in a therapeutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for producing local anesthesia in a mammal range from about 5 mg to about 1000 mg per dose.

The following formulations illustrate representative pharmaceutical compositions of the present invention:

| Ingredient | Quantity |
|---|---|
| Formulation Example 1A-Solution for Injection | |
| Sodium Chloride | 0.9% (0.9 g/100 mL) |
| Methylparaben | 1 mg/mL |
| Compound of formula I | 0.5% (0.5 g/100 mL) |
| Water for injection | to 100 mL |
| Formulation Example 1B-Solution for Injection | |
| Compound of formula I | 20 mg (di-HCl salt) |
| Mannitol | 15.7 mg |
| Sucrose | 37.1 mg |
| 0.1M NaOH | qs. pH 4.7–4.8 |
| 0.1M HCl | qs. pH 4.7–4.8 |
| Water for injection | qs. to 1 mL |
| Formulation Example 1C-Solution for Injection | |
| Compound of formula I | 20 mg (di-HCl salt) |
| 0.85% (Isotonic) Saline Solution | qs. to 1 mL |
| 0.1M NaOH | qs. pH 4.7–4.8 |
| 0.1M HCl | qs. pH 4.7–4.8 |

| Ingredient | Quantity (%) |
|---|---|
| Formulation Example 2-Paste | |
| Compound of formula I | 1 |
| Zinc oxide | 25 |
| Starch | 25 |
| Calamine | 5 |
| White petrolatum | to 100 |
| Formulation Example 3-Ointment | |
| Compound of formula I | 10 |
| White petrolatum | to 100 |
| White wax | 5 |
| Formulation Example 4-Cream | |
| Compound of formula I | 0.5 |

-continued

| Oleaginous phase | |
|---|---|
| Spermaceti | 12.5 |
| White wax | 12.0 |
| Almond oil | 55.5 |
| Aqueous phase | |
| Sodium borate | 0.5 |
| Stronger rose water | 2.5 |
| Purified water | 16.5 |
| Aromatic Rose oil | 0.02 |
| Formulation Example 5-Gel | |
| Compound of formula I | 2 |
| Methocel 90 H.C. 4000 | 0.8 |
| Carbopol 934 | 0.24 |
| Propylene glycol | 16.7 |
| Methylparaben | 0.015 |
| Purified water | to 100 |

Utility

The compounds of formula I are useful for modulating the activity of voltage-gated $Na^+$ channels in mammals, such as humans. Accordingly, the compounds of this invention are useful for treating diseases or medical conditions associated with or modulated by volatage-gated $Na^+$ channels, including the prevention and alleviation of pain, e.g., for topical anesthesia, infiltration anesthesia, field block anesthesia, nerve block anesthesia, spinal anesthesia, epidural anesthesia, post-operative analgesia, post-arthroscopic pain management, inflammatory pain, neuropathic pain. Additionally, the compounds of this invention are also useful for preventing or treating other medical conditions associated with or modulated by voltage-gated $Na^+$ channels, such as depression, seizure (epilepsy), neuroprotection (stroke), protection and recovery from ischemia (Lantos et al, *Arch. Int. Pharmacodyn. Ther.* 331: 179 (1996)), asthma (Hunt et al., *Mayo Clin. Proc.* 71: 361 (1996), rapid heartbeat (Gorgels et al., *Am. J. Cardiol.* 78: 43 (1996)), cardiac arrhythmia (Rosen et al, *Am. Heart J.* 89: 526 (1975), natriuresis (Wyeth et al, *Life Sci.* 60: 473 (1997), proctitis and active distal ulcerative colitis (Arlander et al, *Aliment. Pharmacol. Ther.* 10: 73 (1996)), inflammatory bowel disease and irritable bowel syndrome.

The utility of the compounds of formula I as sodium channel modulators and local anesthetics can be demonstrated using various well-known assays (e.g., the batrachotoxin (BTX) displacement assay (McNeal et al., *J. Med. Chem.* 28: 381 (1985)), patch clamp method (see, Neher and Sakmann, "The Patch Clamp Technique "Scientific American" pp. 44–51 (1992); Hamill et al., *Pfligers Arch.* 391: 85 (1981); intact isolated nerve assay, e.g., isolated frog sciatic nerve; blockage of the cutaneous trunci muscle reflex (CTMR) in guinea pigs (Bulbring et al., *J. Pharmacol. Exp. Therap.* 85: 78–84 (1945); Blight et al, *J. Compar. Neurology* 296: 614–633 (1990); Choi et al., *Life Sci.* 61: PL177–84 (1997)). Additionally, evaluation of motor and sympathetic function during sciatic nerve block in the rat is described, e.g., in Grant et al., *Anesth. Analg.* 75: 889–94 (1992), and Thalhammer et al., *Anesthesiology* 82: 1013–25 (1995). Certain of these assays are described in further detail in the Examples below.

The following synthetic and biological examples are offered to illustrate this invention and are not to be construed in any way as limiting the scope of this invention.

EXAMPLES

In the examples below, the following abbreviations have the following meanings. Abbreviation not defined below have their generally accepted meaning.

| | | |
|---|---|---|
| Boc | = | tert-butoxycarbonyl |
| BTX | = | batrachotoxin |
| DIPEA | = | diisopropylethylamine (Hunig's base) |
| DMF | = | N,N-dimethylformamide |
| DMSO | = | dimethylsulfoxide |
| EGTA | = | ethylene glycol-bis(β-aminoethyl ether) N,N,N',N',-tetraacetic acid |
| EtOAc | = | ethyl acetate |
| EtOH | = | ethanol |
| HATU | = | 6-(7-azabenzotriazol-1-yl)-N,N,N'N'-tetramethyluronium hexafluorophosphate |
| HEPES | = | N-(2-hydroxyethyl)piperazine-N'-(2-ethanesulfonic acid) |
| HOAT | = | 1-hydroxy-7-azabenzotriazole |
| HPLC | = | high performance liquid chromatography |
| MeOH | = | methanol |
| MS | = | mass spectrometry |
| SDS | = | sodium dodecyl sulfate |
| TLC | = | thin layer chromatography |
| TFA | = | trifluoroacetic acid |
| THF | = | tetrahydrofuran |
| UV | = | ultraviolet |

All temperatures reported in the following examples are in degrees Celsius unless otherwise indicated. Also, unless noted otherwise, reagents, starting materials and solvents were purchased from commercial suppliers (such as Aldrich, Fluka, Sigma and the like), and were used without further purification.

Example 1

Synthesis of 7-[(8-Methyl-3-(morpholin-4-ylcarbonylmethyl)-4(3H)-quinazolinon-2-yl) methyl]-16-[(R)-(2-methylphenylaminocarbonyl) prop-1-yl]-1,4,10,13-tetraoxa-7,16-diazacyclooctadecane (Compound 1 in Table I)

Figure 1B:
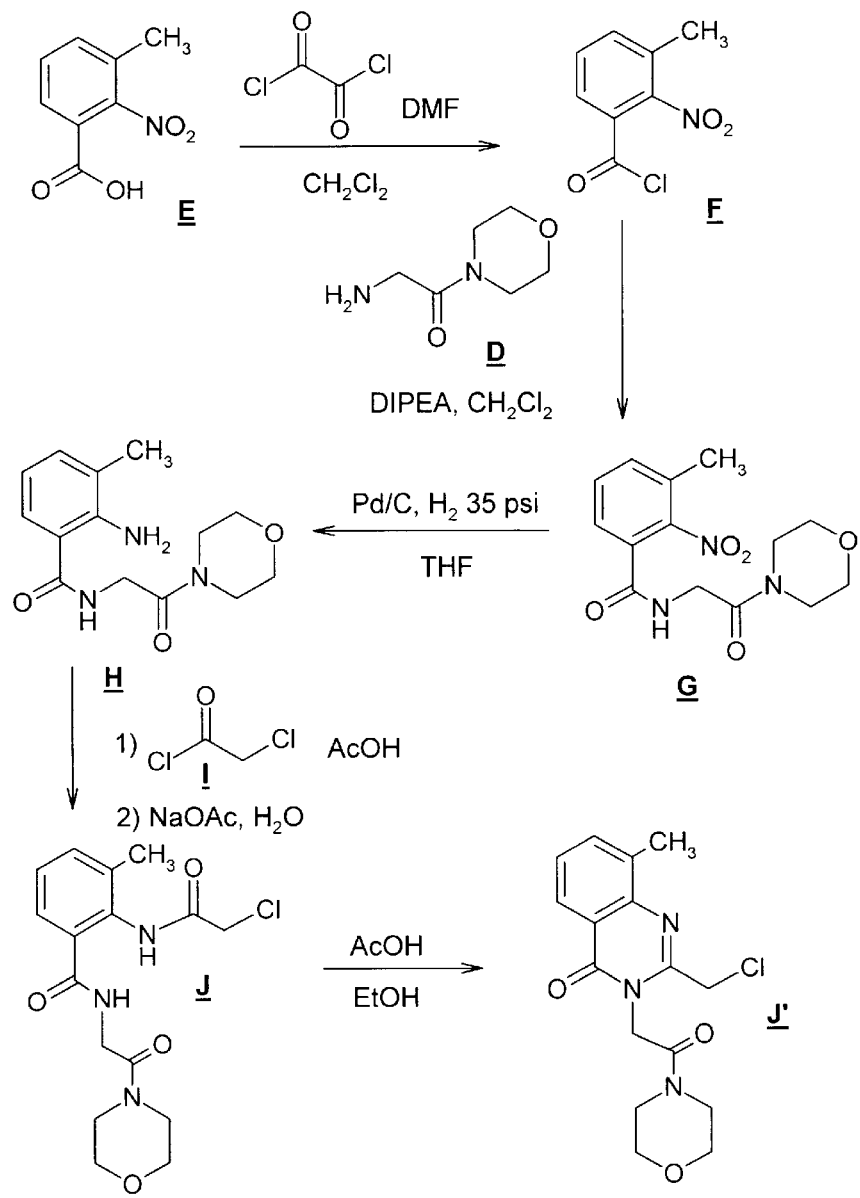
Figure 1C:
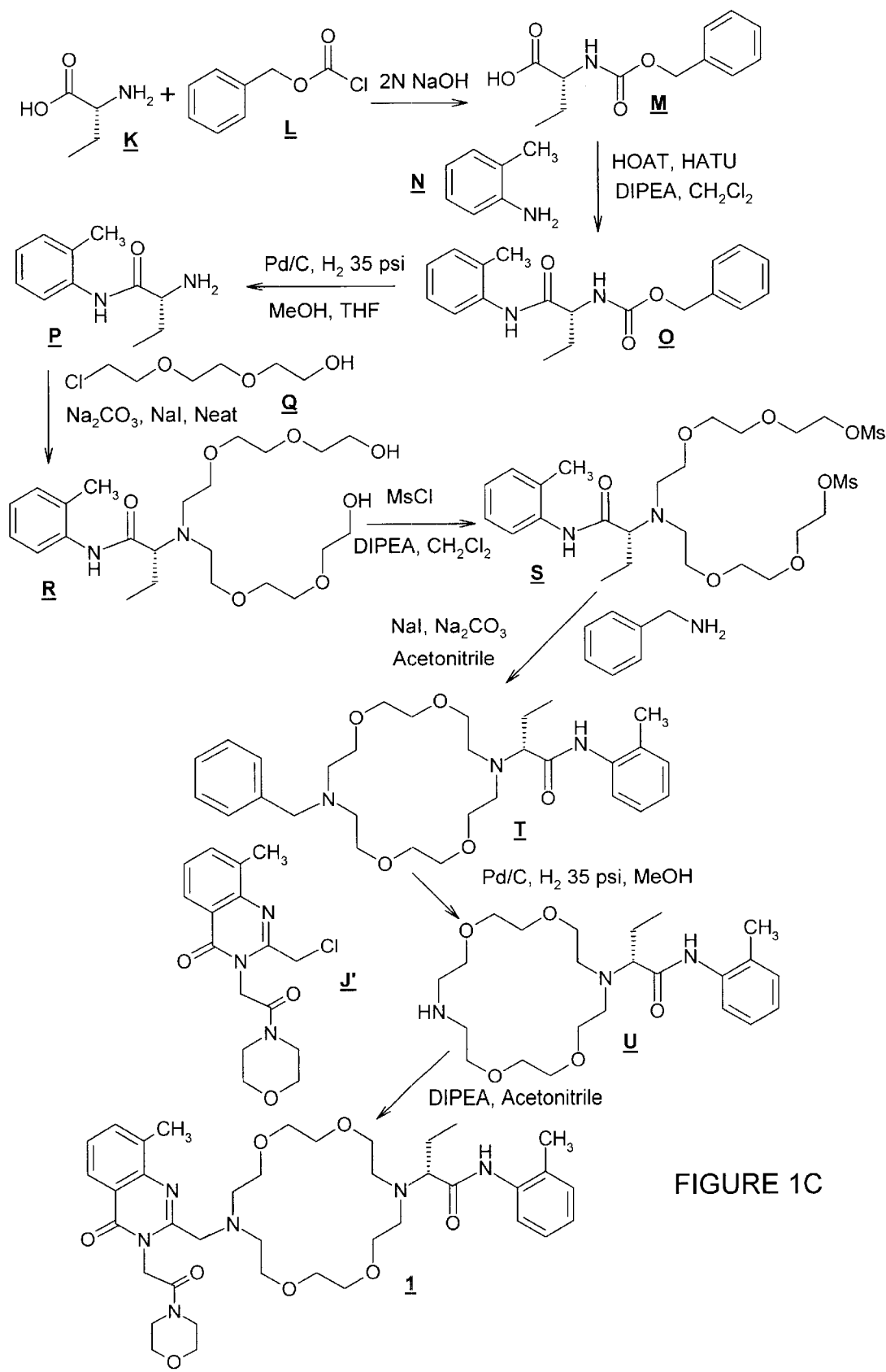

The following synthesis is illustrated in FIGS. 1A, 1B and 1C.

Step 1—Preparation of Compound C

Under $N_2$ in a 1-liter 2-necked round bottom flask equipped with a magnetic stir bar, carbobenzyloxyglycine A (25.8 g, 123 mmoles, 1.0 equiv.), 1-hydroxy-7-azabenzotriazole (HOAT) (3.36 g, 24.7 mmoles, 0.2 equiv.) and N-[(dimethylamino)-1H-1,2,3,-triazolo[4,5-b]pyridin-1-ylmethylene]-N-methylmethanaminium hexafluorophosphate N-oxide (HATU) (46.9 g, 123 mmoles, 1.0 equiv.) were dissolved in N,N-dimethylformamide (DMF) (500 mL). The solution was cooled to 0° C. using an ice bath. N,N-Diisopropylethylamine (DIPEA) (32.2 mL, 185 mmoles, 1.5 equiv.) was added all at once to the stirred reaction mixture. This was followed by the addition of morpholine B (10.8 mL, 123 mmoles, 1.0 equiv.). The reaction was warmed to room temperature and stirring continued for 8 hours. The reaction mixture was poured into a stirred solution of sodium chloride (100 g) in water (3 L) and ice (1.5 L), resulting in precipitation of the product. The suspension was stirred for 1 h after which time the precipitate was isolated by filtration using a Buchner funnel and thoroughly rinsed with water (2 L). The solid was dried in vacuum to provide 31.4 g (91.6%) of compound C as a white solid with >95% purity ($^1$H NMR in DMSO).

On small scale it was advantageous to dry the product quickly using the following method. The solid was dissolved in $CH_2Cl_2$ (1 L) and partitioned with water (100 mL), the layers separated, and the organic layer washed with saturated aqueous NaCl (300 mL) and dried with $MgSO_4$ (50 g), filtered through filter paper, rinsing with $CH_2Cl_2$ (100 mL), concentrated under reduced pressure and place on vacuum line to dry (15 minutes).

Step 2—Preparation of Compound D

Under $N_2$, to a 1-liter Parr bottle was added 10% palladium on carbon (4.0 g) and tetrahydrofuran (THF) (100 mL). Compound C (31.4 g, 113 mmoles, 1.0 equiv.) was dissolved in methanol (MeOH) (100 mL) and THF (300 mL) and added to the Parr bottle. The Parr bottle was degassed under vacuum and filled to 35 psi with hydrogen gas. The shaker was turned on and the reaction allowed to shake for 1 minute, at which time the Parr bottle was degassed under vacuum and filled to 35 psi with hydrogen gas. This was repeated two more times. The reaction was kept under a constant pressure of hydrogen gas (between 25 and 35 psi) for the duration of the reaction time (1 hour). The reaction was monitored by TLC using 90:10 $CH_2Cl_2$:MeOH (starting material $R_f$=0.8 using UV and ninhydrin staining; product $R_f$=0.0 using ninhydrin staining). The reaction mixture was filtered through filter paper using a Buchner funnel and thoroughly rinsed with THF:MeOH (1:1) (300 mL). The filtrate was concentrated to dryness on a rotary evaporator to afford 16.2 g (99.6%) of compound D as a white solid with >95% purity ($^1$H NMR in DMSO).

Step 3—Preparation of Compound F

Under $N_2$ in a 1-liter round bottom flask equipped with a magnetic stir bar, 3-methyl-2-nitrobenzoic acid E (30.0 g, 166 mmoles, 1.0 equiv.) was suspended in $CH_2Cl_2$ (150 mL). The suspension was cooled to 0° C. using an ice bath. Oxalyl chloride (2.0 M in $CH_2Cl_2$, 166 mL, 332 mmoles, 2.0 equiv.) was added to the stirred reaction mixture through a pressure equalizing dropping funnel over 30 minutes. DMF (10 drops) was added dropwise. The reaction mixture was allowed to warm up to room temperature. After 30 minutes the suspended material dissolves and effervescence stops. The reaction was concentrated to dryness on a rotary evaporator. The solid material was redissolved in $CH_2Cl_2$ (200 mL) and was concentrated to dryness on a rotary evaporator to afford 32.9 g (99%) of compound F as an off white solid.

Step 4—Preparation of Compound G

Under $N_2$, in a 1-liter round bottom flask equipped with a magnetic stir bar, compound F (26.9 g, 135 mmoles, 1.2 equiv.) was dissolved in $CH_2Cl_2$ (200 mL). The solution was cooled to 0° C. using an ice bath. DIPEA (29.4 mL, 169 mmoles, 1.5 equiv.) was added all at once to the stirring reaction mixture. This was followed by the dropwise addition of the compound D (16.2 g, 113 mmoles, 1.0 equiv.) dissolved in $CH_2Cl_2$ (200 mL) over one hour using a pressure equalizing dropping funnel. The reaction was warmed to room temperature and stirring continued for 0.5 hour. The reaction mixture was poured into a separatory funnel and washed with saturated sodium bicarbonate ($NaHCO_3$) (250 mL). Washing with $NaHCO_3$ was repeated three times. The organic layer was washed once with saturated sodium chloride (NaCl) (200 mL), dried over anhydrous magnesium sulfate ($MgSO_4$) (20 g), filtered through filter paper using a Buchner funnel and the residue thoroughly rinsed with $CH_2Cl_2$ (200 mL). The filtrate was concentrated to dryness on a rotary evaporator. The product was purified using a silica gel plug. A Buchner funnel was filled with a slurry of silica gel in 98:2 $CH_2Cl_2$:MeOH (200 mL) and a solution of impure product in 98:2 $CH_2Cl_2$:MeOH (10 mL) was loaded onto the plug and a vacuum was applied to draw the solution into the silica gel plug. The plug was eluted with 98:2 CH$_2$Cl$_2$:MeOH (500 mL) using vacuum to pull solvent through the plug until all of the product had eluted. The pure fractions were combined and concentrated to dryness on a rotary evaporator to afford 32.8 g (95.0%) of compound G as a white solid with >95% purity ($^1$H NMR in DMSO). During the above procedure, the product was monitored by TLC using 90:10 CH$_2$Cl$_2$:MeOH (starting material as carboxylic acid R$_f$=0.25 using UV; product R$_f$=0.6 using UV and ninhydrin staining).

Step 5—Preparation of Compound H

Under N$_2$, to a 1-liter Parr bottle was added 10% palladium on activated carbon (4.5 g) and tetrahydrofuran (THF) (100 mL). Compound G (35.5 g, 116 mmoles, 1.0 equiv.) was dissolved in THF (300 mL) (starting material will precipitate out of THF if any MeOH is added) and added to the Parr bottle. The Parr bottle was degassed under vacuum and filled to 35 psi with hydrogen gas. The shaker was turned on and the reaction allowed to shake for 1 minute, at which time the Parr bottle was degassed under vacuum and filled to 35 psi with hydrogen gas. This was repeated two more times. The reaction was kept under a constant pressure of hydrogen gas (between 25 and 35 psi) for the duration of the reaction time (2 hours). The reaction was monitored by TLC using 90:10 CH$_2$Cl$_2$:MeOH (starting material R$_f$=0.6 using UV and ninhydrin staining; product R$_f$=0.55 using UV and ninhydrin staining). The reaction mixture was filtered through filter paper using a Buchner funnel and the residue thoroughly rinsed with THF (300 mL). The filtrate was concentrated to dryness on a rotary evaporator to afford 31.83 g (99.1%) of compound H as a white solid with >95% purity ($^1$H NMR in DMSO).

Step 6—Preparation of Compound J

Under N$_2$ in a 1-liter 3-necked round bottom flask equipped with a magnetic stir bar, compound H (20.0 g, 72.2 mmoles, 1.0 equiv.) was dissolved in acetic acid (64.0 mL). The round bottom was cooled to 10° C. using a cold water bath (cooling is desirable to control reaction exothermicity, but it is necessary to avoid freezing the acetic acid solution). Chloroacetyl chloride I (6.33 mL, 79.4 mmoles, 1.1 equiv.) was added all at once to the stirring reaction mixture. This was immediately followed by the addition of a solution of sodium acetate (24.8 g) in water (126 mL) (the product precipitates out at this point as a white solid). The reaction was warmed to room temperature while stirring for 20 minutes. Manual shaking was applied periodically to break up thick clumps of precipitate. The mixture was filtered through filter paper using a Buchner funnel and the solid thoroughly rinsed with water (3 L). The solid was dried in vacuum to afford 20.12 g (78.8%) of compound J as a white solid with 99% purity ($^1$H NMR in DMSO).

On small scale it was advantageous to dry the product quickly using the following method. The solid was suspended in diethyl ether and stirred vigorously to dissolve residual water and acetic acid. If an aqueous layer formed, it was removed by decanting. The solid was isolated by filtration. The ether wash may be repeated once or twice more if necessary.

Step 7—Preparation of Compound J'

A suspension of compound J (30.0 g, 84.9 mmol) in acetic acid (80 mL) and EtOH (80 mL) was heated at 85° C. After a few minutes heating, a homogeneous solution was obtained and the stirring was continued at 85° C. for 12 h. Upon cooling to room temperature, the product crystallized. The solid was filtered and washed with EtOH. The filtrate was concentrated and a second crop of crystals was obtained by recrystallization from ethanol. The solid was filtered and washed with EtOH. The filtrate was concentrated and a third crop of crystals was obtained by recrystalization from ethanol. The three crops of crystals (crop 1=17.8 g, crop 2=3.6 g, crop 3=1.3 g) were determined to be pure by HPLC analysis and combined to give compound J' as a white crystalline solid (22.7 g, 80%). During the above procedure, the reaction was monitored by TLC using 70:30 ethyl acetate:hexanes with detection by UV absorbance (product R$_f$=0.38). The reaction can also be monitored by HPLC and product purity was determined by HPLC using a Zorbax Bonus RP (5 µm) column (2.1 mm×50 mm) with a gradient of 10 to 70% acetonitrile/0.2% TFA in water/0.2% TFA over 5.0 min with a flow rate of 0.5 mL/min and detection by UV absorbency at 214 nm. Under these conditions, the product eluted at 3.4 min and the starting material eluted at 2.1 min.

Step 8—Preparation of Compound M

Under N$_2$ in a 2-liter 3-necked round bottom flask equipped with a magnetic stir bar, (R)-(+)-2-aminobutyric acid K (100 g, 970 mmoles, 1.0 equiv.) was dissolved in 2 N sodium hydroxide (NaOH) (500.0 mL). The solution was cooled to 0° C. using an ice bath. Benzyl chloroformate L (166.0 mL, 1160 mmoles, 1.2 equiv.) and 2 N NaOH (800 mL) were added alternately in small portions (approximately ten portions each). The reaction mixture should remain alkaline: if necessary more 2 N NaOH is added. The temperature of the reaction mixture was kept between 5 and 10° C. by the rate of addition of the reactants. Addition over approximately 1.5 hours allows the temperature to remain in this range. The ice bath was then replaced by a 20° C. water bath, and vigorous stirring was continued for an additional hour. The alkaline solution was extracted three times with ether (500 mL each); the ether extracts were discarded. The alkaline layer was made acidic by the addition of 3 N hydrochloric acid (HCl) (400 mL) and extracted three times with ether (500 mL each). The combined ether layers were washed once with saturated sodium chloride (NaCl) (400 mL), dried over anhydrous magnesium sulfate (MgSO$_4$) (80 g), filtered through filter paper using a Buchner funnel and the residue thoroughly rinsed with ether (500 mL). The filtrate was concentrated to dryness on a rotary evaporator to afford 228 g (99%) of compound M as a white solid with >95% purity ($^1$H NMR in DMSO).

Step 9—Preparation of Compound O

Under N$_2$ in a 1-liter 2-necked round bottom flask equipped with a magnetic stir bar, carbobenzyloxy-(R)-2-aminobutyric acid M (40.0 g, 169 mmoles, 1.0 equiv.), 1-hydroxy-7-azabenzotriazole (HOAT) (4.59 g, 33.8 mmoles, 0.2 equiv.) and N-[(dimethylamino)-1H-1,2,3,-triazolo[4,5-b]pyridin-1-ylmethylene]-N-methylmethanaminium hexafluorophosphate N-oxide (HATU) (64.2 g, 169 mmoles, 1.0 equiv.) were dissolved in N,N-dimethylformamide (DMF) (350 mL). The solution was cooled to 0° C. using an ice bath. N,N-diisopropylethylamine (DIPEA) (44.1 mL, 253 mmoles, 1.5 equiv.) was added all at once to the stirred reaction mixture. This was followed by the addition of o-toluidine N (18.0 mL, 169 mmoles, 1.0 equiv.). The reaction was warmed to room temperature and stirring continued for 8 hours. The reaction mixture was poured into a stirred solution of sodium chloride (500 g) in water (3 L) and ice (1.5 L), causing the product to precipitate. The precipitate isolated by filtration using a Buchner funnel and thoroughly rinsed with water (2 L). The solid was dried in vacuum to afford 51.2 g (93%) of compound O as a white solid with >95% purity ($^1$H NMR in DMSO).

On small scale it was advantageous to dry the product quickly using the following method. The solid was dissolved in CH$_2$Cl$_2$ (1-liter) and washed with water (100 mL) followed by saturated NaCl (300 mL), the CH$_2$Cl$_2$ layer was dried with MgSO$_4$ (50 g), filtered through filter paper, the residue rinsed with CH$_2$Cl$_2$ (100 mL), concentrated under reduced pressure and placed on vacuum line to dry (15 minutes).

Step 10—Preparation of Compound P

Under N$_2$, to a 1-liter Parr bottle was added 10% palladium on activated carbon (5.8 g) and tetrahydrofuran (THF) (100 mL). Compound O (55.0 g, 162 mmoles, 1.0 equiv.) was dissolved in MeOH (250 mL) and THF (200 mL) and added to the Parr bottle. The Parr bottle was degassed under vacuum and filled to 35 psi with hydrogen gas. The shaker was turned on and the reaction allowed to shake for 1 minute, at which time the Parr bottle was degassed under vacuum and filled to 35 psi with hydrogen gas. This was repeated two more times. The reaction was kept under a constant pressure of hydrogen gas (between 25 and 35 psi) for the duration of the reaction time (1 hour). The reaction was monitored by TLC using 50:50 ethyl acetate:hexanes (starting material $R_f$=0.8 using UV and ninhydrin staining; product $R_f$=0.0 using UV and ninhydrin staining). The reaction mixture was filtered through filter paper using a Buchner funnel and thoroughly rinsed with 50% THF, 50% MeOH (300 mL). The filtrate was concentrated to dryness on a rotary evaporator to afford 32.6 g (98%) of compound P as a white solid with >95% purity ($^1$H NMR in DMSO).

In the above procedure, the starting material O was dissolved by heating in THF/MeOH at the concentrations described and remained in solution for some time, however, it did begin to crystallize over time. Therefore, it may be advantageous to carry out this reaction at slightly elevated temperature or to use a solvent mixture in which the starting material is more soluble.

Step 11—Preparation of Compound R

In a 3-neck 1000 mL flask equipped with a mechanical stirrer, amine P (113 g, 587 mmol), 2-[2-(chloroethoxy) ethoxy]ethanol O (188 mL, 218 g, 1290 mmol, 2.2 equiv.), sodium iodide (88.0 g, 587 mmol, 1.0 eq), and sodium carbonate (218 g, 2050 mmol, 3.5 equiv.) were combined and heated to 120° C. Evolution of gas was observed during heating and a red color developed. After 8 h, the reaction was cooled to room temperature and transferred to a separatory funnel. The mixture was dissolved by shaking with a mixture of 1.5 L ethyl acetate and 1.5 L water. The layers were separated and the ethyl acetate was washed with 1000 mL water. The aqueous layers were combined and extracted with 500 mL ethyl acetate. The ethyl acetate layers were combined and washed with saturated aqueous sodium bicarbonate (1 L) and then extracted with two 700 mL portions of 1 N HCl. The aqueous acid layers were combined and washed two times with 1000 mL portions of ethyl acetate. The aqueous acid was then made basic by dropwise addition of 3.0 N NaOH until the pH reached 8.0. The resulting cloudy suspension was then extracted with 1000 mL ethyl acetate. The pH of the aqueous layer was adjusted up to 9.0 and extracted twice with 1000 mL portions of ethyl acetate. These ethyl acetate layers (extracts of basic aqueous solution) were combined and dried over anhydrous magnesium sulfate (MgSO$_4$) (50 g), filtered through filter paper using a Buchner funnel and the residue thoroughly rinsed with ethyl acetate (600 mL). The filtrate was concentrated on a rotary evaporator to give a 229 g (86%) of diol R as a pale yellow oil with >85% purity (HPLC, 214 nm, NMR). During this procedure, the reaction was monitored by TLC using 90:10 CH$_2$Cl$_2$:MeOH with detection by UV absorbance (product $R_f$=0.58). The reaction was also monitored and product purity assessed by HPLC using a Zorbax Bonus RP (5 µm) column (2.1 mm×50 mm) with a gradient of 10 to 70% acetonitrile/0.2% TFA in water/0.2% TFA over 5.0 min with a flow rate of 0.5 mL/min and detection by UV absorbency at 214 nm. Under these conditions the product eluted at 1.8 min.

Step 12—Preparation of Compound S

Under N$_2$, in a 5000-mL three-neck flask equipped with a magnetic stir bar, diol R (229 g, 502 mmoles, 1.0 equiv.) was dissolved in CH$_2$Cl$_2$ (3000 mL). The solution was cooled to −10° C. using an ice/isopropanol bath. DIPEA (210 mL, 1200 mmoles, 2.4 equiv.) was added all at once to the stirring reaction mixture. This was followed by the dropwise addition of methanesulfonyl chloride (81 mL, 1040 mmoles, 2.07 equiv.). Upon completion of addition, TLC indicated that the reaction was complete. Saturated aqueous sodium bicarbonate (1000 mL) was added to the cold reaction mixture with vigorous stirring, and the mixture was transferred to a separatory funnel. The layers were separated and the methylene chloride layer was extracted with a second portion (500 mL) of saturated aqueous sodium bicarbonate. The aqueous layers were combined and extracted once with CH$_2$Cl$_2$ (600 mL). The organic layers were combined, washed with saturated aqueous sodium chloride (500 mL), dried over anhydrous magnesium sulfate (MgSO$_4$) (50 g), filtered through filter paper using a Buchner funnel and the residue thoroughly rinsed with CH$_2$Cl$_2$ (100 mL). The filtrate was concentrated to dryness on a rotary evaporator to yield a brown oil. This oil was purified in six batches of approximately 50 g each by filtering through plugs of silica as follows. A Buchner funnel was filled with a slurry of silica gel in CH$_2$Cl$_2$ (450 mL). A solution of impure product in CH$_2$Cl$_2$ (60 mL) was loaded onto the plug and a vacuum was applied to draw the solution into the silica gel plug. The plug was washed with CH$_2$Cl$_2$ (400 mL) and eluted with 99:1 CH$_2$Cl$_2$:MeOH (600 mL) using vacuum to pull solvent through the plug until all of the product had eluted. The pure fractions were combined and concentrated to dryness on a rotary evaporator. This process was repeated once to afford the product in 96% purity. The pure fractions from all silica plugs were combined and concentrated to afford 234 g (76%) of compound S as a yellow oil with >97% purity (HPLC, 214 nm, NMR CDCl$_3$. During this procedure, the reaction was monitored by TLC using 90:10 CH$_2$Cl$_2$:MeOH with detection by UV absorbance (starting material $R_f$=0.58; product $R_f$=0.74). The reaction was also monitored and the purity of the product determined by HPLC using a Zorbax Bonus RP (5 µm) column (2.1 mm×50 mm) with a gradient of 10 to 70% acetonitrile/0.2% TFA in water/0.2% TFA over 5.0 min with a flow rate of 0.5 mL/min and detection by UV absorbency at 214 nm. Under these conditions, the starting material eluted at 1.8 min, and the product eluted at 2.8 min.

Step 13—Preparation of Compound T

Divided equally between two 5000-mL 3-neck round bottom flasks equipped with mechanical stirrers, thermometers and reflux condensors, dimesylate S (234 g, 381 mmol, 1.15 equiv.) and benzylamine (36.2 mL, 35.5 g, 331 mmol, 1.0 equiv) were dissolved in acetonitrile (6000 mL). Sodium iodide (109 g, 723 mmol, 2.2 equiv) and sodium carbonate (158 g, 1490 mmol, 4.5 equiv) were added (half of each to each of the two flasks) and the suspensions were heated between 60 and 70° C. for 40 h. The suspensions were combined and filtered through filter paper using a Buchner funnel and the residue thoroughly rinsed with acetonitrile (800 mL). The filtrate was concentrated in vacuo to a thick yellow oil and redissolved in ethyl acetate (1000 mL). The suspension was washed with two 1 L portions of saturated sodium bicarbonate followed by 250 mL of saturated aqueous sodium chloride. The ethyl acetate layer was then shaken with 500 mL of 0.2 N HCl. The pH was gradually lowered by portionwise addition of 1.0 N HCl followed by shaking until the aqueous layer had a pH of 4. The layers were separated. The ethyl acetate layer was extracted with a second portion of 0.2 N HCl (500 mL), again adding portions of 1.0 N HCl and shaking until the pH reached 3. This process was repeated a third time, bringing the final aqueous extract to a pH of 1. HPLC confirmed that no product remained in the ethyl acetate layer and this layer was discarded. The aqueous acid layers were combined and a milky precipitate formed. The pH of the combined aqueous layers was reduced to 3 by dropwise addition of concentrated HCl at which point a clear solution was obtained. Activated carbon (50 g decolorizing carbon, Aldrich # 16155-1) was added and stirred for 10 min. Activated carbon was removed by filtration through a buchner funnel (although it would have been preferable to have continued the charcoal treatment in aqueous acid at this point, the product was extracted into the organic in order to avoid leaving the product exposed to aqueous acid overnight due to concerns about racemization at low pH). The aqueous acid was made basic by dropwise addition of 6.0 N NaOH until the pH reached 6.0. The resulting cloudy suspension was then extracted with 300 mL ethyl acetate. The pH of the aqueous layer was adjusted up to 8.0 and extracted with 600 mL ethyl acetate. These ethyl acetate layers (extracts of basic aqueous solution) were combined and concentrated to give 155 g of crude product. Purity was 74% by HPLC. The crude product was dissolved in the minimal amount of 1 N HCl (approximately 1 L). Upon complete dissolution of product, the pH reached 3. To this solution was added 236 g of decolorizing carbon in three batches followed by 30 g of DARCO G60. The activated carbon was removed by filtration using a Buchner funnel and the residue throroughly washed with 0.1 N HCl (300 mL). To the filtrate was added 130 g DARCO G60. After 10 min, the DARCO was removed by filtration using a Buchner funnel and the residue thoroughly washed with 0.1 N HCl (300 mL). The filtrate was then made basic by dropwise addition of 6.0 N NaOH until the pH reached 7.0. The resulting cloudy suspension was then extracted with 500 mL ethyl acetate. The pH of the aqueous layer was adjusted back up to 7.0 and extracted with 500 mL ethyl acetate. These ethyl acetate layers (extracts of neutral aqueous solution) showed high purity by HPLC and were combined, washed with 400 mL saturated aqueous sodium bicarbonate, and dried over anhydrous magnesium sulfate ($MgSO_4$) (25 g), filtered through filter paper using a Buchner funnel and the residue thoroughly rinsed with ethyl acetate (200 mL). The filtrate was concentrated on a rotary evaporator to give a 62 g (35%) of compound T as a colorless oil, 96% pure by HPLC. During the above procedure, the reaction was monitored by TLC using 90:10 $CH_2Cl_2$:MeOH with detection by UV absorbance (product $R_f$=0.48). The reaction was also monitored and the purity of the product determined by HPLC using a Zorbax Bonus RP (5 $\mu$m) column (2.1 mm×50 mm) with a gradient of 10 to 70% acetonitrile/0.2% TFA in water/0.2% TFA over 5.0 min with a flow rate of 0.5 mL/min and detection by UV absorbency at 214 nm. Under these conditions, starting material eluted at 2.8 min, but was rapidly converted to a diiodide which eluted at 3.8 min; and the product eluted at 2.1 min.

Step 14—Preparation of Compound U

Under $N_2$, to a 1000-mL Parr bottle was added 10% palladium on activated carbon (6.2 g) and methanol (MeOH) (75 mL). Compound T (62.4 g, 118 mmoles) was dissolved in MeOH (75 mL) and added to the Parr bottle. The Parr bottle was degassed under vacuum and filled to 40 psi with hydrogen gas. The shaker was turned on and the reaction allowed to shake for 1 minute, at which time the Parr bottle was degassed under vacuum and filled to 40 psi with hydrogen gas. This was repeated two more times. The reaction was kept under a constant pressure of hydrogen gas (between 35 and 40 psi) for the duration of the reaction time (4 hours). The reaction mixture was filtered through filter paper using a Buchner funnel and thoroughly rinsed with MeOH (100 mL). The filtrate was concentrated to dryness on a rotary evaporator to afford 54.5 g (>98%) of compound U as a colorless oil with >95% purity (HPLC). During this procedure, the reaction was monitored by TLC using 10:90 MeOH:$CH_2Cl_2$ (starting material $R_f$=0.55 using UV and ninhydrin staining; product $R_f$=0.25 using UV and ninhydrin staining). The reaction was also monitored and the product purity determined by HPLC using a Zorbax Bonus RP (5 $\mu$m) column (2.1 mm×50 mm) with a gradient of 2 to 50% acetonitrile/0.2% TFA in water/0.2% TFA over 5.0 min with a flow rate of 0.5 mL/min and detection by UV absorbency at 214 nm. Under these conditions, the starting material eluted at 3.0 min and the product eluted at 2.2 min.

Step 15—Preparation of Compound 1

A mixture of compound J' (37.0 g, 110 mmol, 1.1 equiv), compound U (43.7 g, 100 mmol, 1.0 equiv) and diisopropylethylamine (20.0 mL, 129 mmol, 1.15 equiv) in acetonitrile (400 mL) was heated at 65° C. for 15 h. HPLC analysis indicated that the reaction was incomplete. An additional 3.5 g of compound J' was added and the reaction was allowed to proceed an addtional 15 h. HPLC analysis indicated that the reaction was complete. The solution was concentrated in vacuo to an oil and redissolved in ethyl acetate (600 mL). The ethyl acetate solution was washed with water (3×150 mL). The aqueous washes were combined and extracted with 100 mL ethyl acetate. The ethyl acetate phases were combined and extracted with portions of 1.0 N HCl (500 mL followed by 250 mL). The aqueous acid layers were combined and washed twice with 150 mL portions of ethyl acetate. The yellow acidic aqueous layer was treated with 29 g of activated carbon. The mixture was stirred vigorously for 30 min and then filtered. The colorless filtrate was treated with 1.0 N NaOH by dropwise addition until the pH had reached 4.5 and a milky suspension had formed. This suspension was extracted with 400 mL ethyl acetate. The aqueous layer was further treated by dropwise addition of 1.0 N NaOH until the pH reached 6.0. The resulting cloudy suspension was extracted with 250 mL ethyl acetate. The aqueous layer was further treated by dropwise addition of 1.0 N NaOH until the pH reached 8.5 and extracted with 250 mL ethyl acetate. These ethyl acetate layers (extracts of basic aqueous solution) were combined, dried over anhydrous magnesium sulfate ($MgSO_4$) (20 g), filtered through filter paper using a Buchner funnel and the residue thoroughly rinsed with ethyl acetate (100 mL). The filtrate was concentrated on a rotary evaporator to afford 62 g of compound 1 as pale yellow oil (84%), 94% pure by HPLC. This material was further purified by silica gel chromatography in two batches of approximately equal mass. For each batch, a Buchner funnel was filled with a slurry of silica gel in $CH_2Cl_2$ (400 mL). A solution of impure product in $CH_2Cl_2$ (25 mL) was loaded onto the plug and a vacuum was applied to draw the solution into the silica gel plug. The plug was washed with $CH_2Cl_2$ (1000 mL) and eluted with 99:1 $CH_2Cl_2$:MeOH (2000 ml) followed by 98:2 $CH_2Cl_2$:MeOH (2000 mL) using vacuum to pull solvent through the plug until all of the product had eluted. The pure fractions from both silica plugs were combined and concentrated to dryness on a rotary evaporator to afford 46.5 g (63%) of the product as a colorless oil, >99% pure by HPLC. MS M+H=737.7. During this procedure, the reaction was monitored by TLC using 90:10 $CH_2Cl_2$:MeOH with detection by UV absorbance (product $R_f$=0.60). The reaction was also monitored and the product purity determined by HPLC using a Zorbax Bonus RP (5 μm) column (2.1 mm×50 mm) with a gradient of 10 to 70% acetonitrile/0.2% TFA in water/0.2% TFA over 5.0 min with a flow rate of 0.5 mL/min and detection by UV absorbency at 214 nm. Under these conditions, the product eluted at 2.7 min and the starting materials eluted at 3.4 min (J') and 1.3 min (U).

Alternatively, intermediate H was prepared by the following procedure:

Step 1—Preparation of N-(2-Amino-3-methylbenzoyl) glycine Methyl Ester

2-Amino-3-methylbenzoic acid (100 g, 662 mmoles, 1.0 equiv.), glycine methyl ester hydrochloride (100 g, 797 mmoles, 1.2 equiv), and diisopropylethylamine (175 mL, 1000 mmoles, 1.5 equiv) were dissolved in acetonitrile (860 mL) and chilled to 0° C. 1-[3-(dimethyhlaminopropyl]-3-ethylcarbodiimide hydrochloride (141 g, 736 mmoles, 1.11 equiv.) was added in one portion. The reaction was stirred and allowed to warm slowly to room temperature. After 16 h, the reaction was concentrated in vacuo and diluted with ethyl acetate and washed with saturated aqueous ammonium chloride followed by saturated aqueous sodium chloride. Significant amounts of product remained in the aqueous layers. These were washed with additional portions of ethyl acetate. All ethyl acetate layers were combined, dried ($Na_2SO_4$) and concentrated. The product was recrystallized from ethyl acetate/hexanes to yield a first crop of 118 g (80%). Additional product present in the mother liquor was purified by silica gel chromatography to afford an addtional 5.0 g (4%). This reaction was monitored by TLC using 50:50 ethyl acetate:hexanes with detection by UV absorbance (product $R_f$=0.46).

Step 2—Preparation of Compound H

N-(2-Amino-3-methylbenzoyl)glycine methyl ester (123 g, 554 mmol) was combined with morpholine (530 mL, 6070 mmol), the mixture was stirred at 130° C. for 16 h. Excess morpholine was removed under vacuum and the residue was treated with methanol to precipitate the product (ethyl acetate was also effective at precipitating the product). The precipitate was collected by filtration and dried to afford 68 g of compound H in good purity. The filtrate was concentrated and filtered through silica gel. Product was eluted with ethyl acetate and precipitated from the pure fractions. This product was collected by filtration. The filtrate was concentrated and treated with methanol to precipitate additional product. The filtrate was again concentrated and treated with methanol to precipitate additional product. All crops of product were evaluated for purity and were found to be of excellent quality. All crops were combined to afford 102 g (67%) of compound H which was characterized by NMR. This reaction was monitored by TLC using 90:10 $CH_2Cl_2$:MeOH (product $R_f$=0.55 using UV and ninhydrin staining).

Example 2A

Synthesis of 7-[(8-Methyl-3-(morpholin-4-ylcarbonylmethyl)-4(3H)-quinazolinon-2-yl) methyl]-16-[(R)-(2-methylphenylaminocarbonyl) prop-1-yl]-1,4,10,13-tetraoxa-7,16-diazacyclooctadecane (Compound 1 in Table I)

Figure 2:
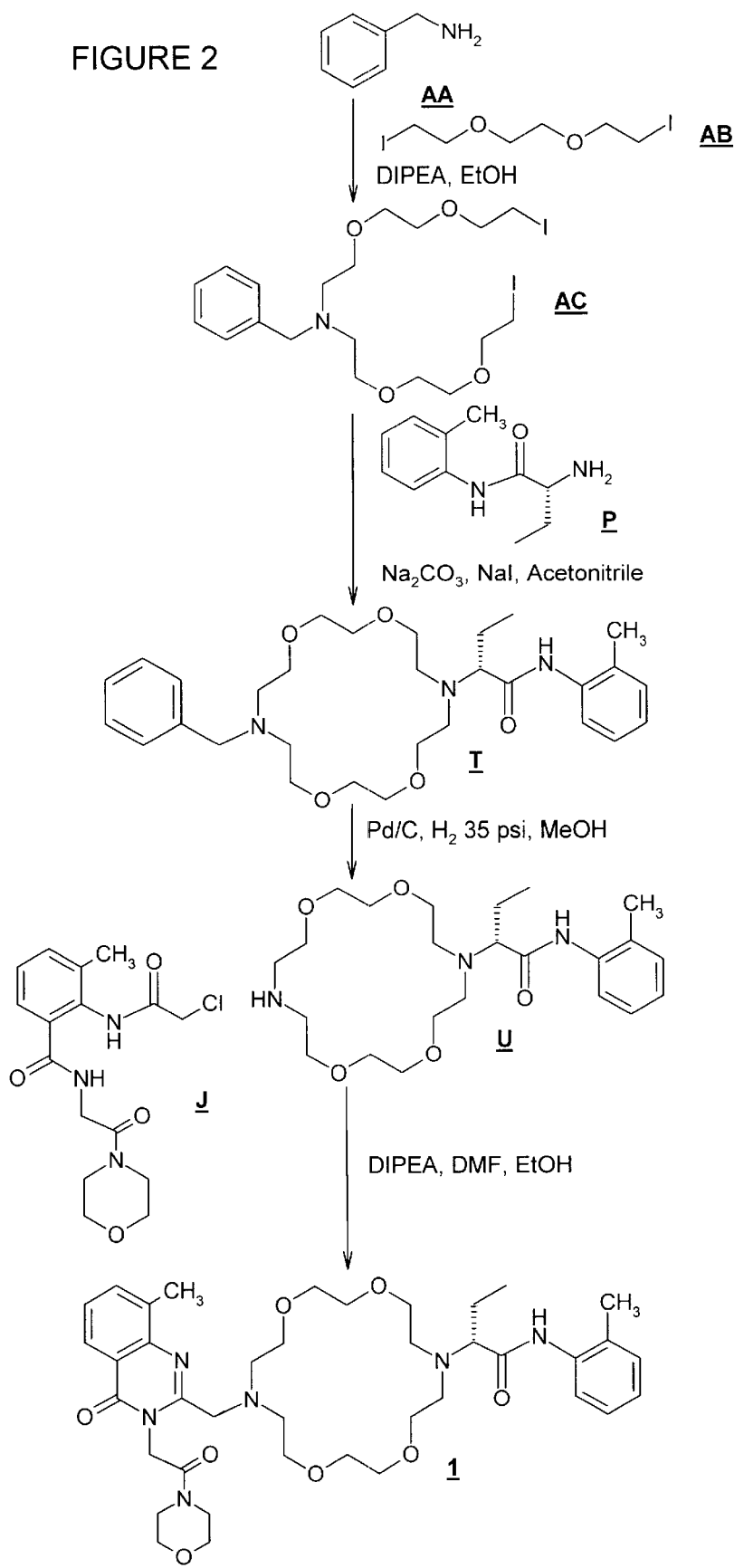
FIG. 2 illustrates an alternative systhesis of a representative compound of this invention using an intermediate of formula II.

The following is an alternative synthesis of Compound 1. This synthesis is illustrated in FIG. 2.

Step 1—Preparation of Compound AC

Benzylamine AA (40.0 g, 373 mmol, 1.0 equiv.) and 1,2-bis-(2-iodoethoxy)ethane AB (414.3 g, 1120 mmol, 3.0 equiv.) were dissolved in ethanol (EtOH) (200 mL) contained in a 1-liter 1-necked round bottom flask equipped with a magnetic stir bar and reflux condenser. NN-diisopropylethylamine (DIPEA) (162.6 mL, 933 mmol, 2.5 equiv.) was added and the reaction mixture was warmed to 70° C. After 8 h, the reaction mixture was cooled to room temperature at which time crystallization of byproducts occurred. To help precipitation of these salts, hexanes (500 mL) was added to the stirred suspension. The salts were filtered off using a Buchner funnel and rinsed with hexanes (1 L). The filtrate was concentrated to a thick oil on a rotary evaporator. The residue was purified using a silica gel plug to give compound AC (63.4 g, 28.7%) as a yellow oil with >95% purity.

Step 2—Preparation of Compound T

A solution of compound AC (9.6 g, 50 mmol, 1.0 equiv.), compound 1P (36.8 g, 62.2 mmol, 1.25 equiv.), sodium iodide (3.8 g, 25 mmol, 0.5 equiv.), and sodium carbonate (26.5 g, 250 mmol, 5.0 equiv.) in acetonitrile (992 mL, 0.05 M) was divided among 32 sealed tubes each equipped with a magnetic stir bar under nitrogen. The reaction mixture was warmed to 120° C. and stirring was continued for 12 h. The reaction mixture was cooled to room temperature. The contents of the tubes were poured into a round bottom flask (2 L) and the tubes were thoroughly rinsed with acetonitrile to recover all residue (including the insoluble salts). The suspension was concentrated to a thick suspension and the residue was partitioned between water (200 mL) and EtOAc (300 mL). The water layer was extracted with EtOAc (100 mL). The combined organic layers were dried over anhydrous magnesium sulfate ($MgSO_4$) (30 g), filtered through filter paper using a Buchner funnel and the residue was thoroughly rinsed with EtOAc (100 mL). The filtrate was concentrated to dryness on a rotary evaporator. The resulting material was purified by preparatory HPLC using a Varian ROOPK201K8 (8 μm) column (100 mm×250 mm) with a flow rate of 250 mL/min. Product eluted at 28% acetonitrile/water and was detected by UV absorbency at 214 nm. Product was isolated by removing the water:acetonitrile mixture on a rotary evaporator and partitioning the residue with 3 N NaOH (50 mL). The product was extracted with EtOAc (2×200 mL) and the combined organic layers were washed once with saturated sodium chloride (NaCl) (100 mL), dried over anhydrous magnesium sulfate ($MgSO_4$) (40 g), and filtered through filter paper using a Buchner funnel. The residue was thoroughly rinsed with EtOAc (100 mL) and the filtrate was concentrated to dryness on a rotary evaporator to give compound T (11.3 g, 42.8%) as a clear oil with >95% purity.

Step 3—Preparation of Compound U

Compound T (5.0 g, 9.5 mmol, 1.0 equiv.) was dissolved in MeOH (100 mL) and added to a 1-liter Parr bottle containing 10% palladium on activated carbon (5.0 g) and methanol (MeOH) (100 mL) under nitrogen. The Parr bottle was degassed under vacuum and filled with hydrogen gas. Debenzylation was carried out at 35 psi for 12 h. The reaction mixture was filtered through filter paper using a Buchner funnel and thoroughly rinsed with MeOH (300 mL). The filtrate was concentrated to dryness on a rotary evaporator to give compound U (3.5 g, 85%) as a white solid with >95% purity.

Step 4—Preparation of Compound 1

Compound J (8.9 g, 25.3 mmol, 1.3 equiv.), compound U (8.5 g, 19.5 mmol, 1.0 equiv.), EtOH (15 mL), DMF (18 mL)

and N,N-diisopropylethylamine (DIPEA) (5.1 mL, 29.2 mmol, 1.5 equiv.) were combined and then divided equally into three pressure tubes, each containing a magnetic stir bar. The tubes were sealed and heated to 120° C. with stirring for 5 h. The contents of the tubes were combined in a separatory funnel and partitioned between 1 N HCl (200 mL) and EtOAc (500 mL). The aqueous layer was washed with EtOAc (4×400 mL). The acidic layer was made basic (pH >10) with the addition of 3 N NaOH (300 mL) and extracted with EtOAc (1×400 mL). The EtOAc layer was washed once with saturated sodium bicarbonate (NaHCO$_3$) (250 mL) and once with saturated sodium chloride (NaCl) (200 mL). The solution was dried over anhydrous magnesium sulfate (MgSO$_4$) (50 g), filtered through filter paper using a Buchner funnel and the residue thoroughly rinsed with EtOAc (200 mL). The filtrate was concentrated to dryness on a rotary evaporator. The product was partially purified using a silica gel plug with an elution gradient: CH$_2$Cl$_2$ (500 mL), 2:98 MeOH:CH$_2$Cl$_2$ (500 mL) and then 5:95 MeOH:CH$_2$Cl$_2$ (500 mL). The organic solvents were concentrated and the resulting material was loaded onto a preparatory HPLC for further purification using a Varian ROOPK201K8 (8 μm) column (100 mm×250 mm) with a flow rate of 250 mL/min. The product eluted with 28% acetonitrile/water and was detected by UV absorbency at 214 nm. The water:acetonitrile mixture was concentrated on a rotary evaporator. The residue was partitioned with 3 N NaOH (25 mL) and extracted with EtOAc (2×150 mL). The combined EtOAc layers were washed with saturated sodium chloride (NaCl) (100 mL), dried over anhydrous magnesium sulfate (MgSO$_4$) (20 g), and filtered through filter paper using a Buchner funnel. The filtrate was concentrated to dryness on a rotary evaporator to give compound 1 (6.0 g, 41.9%) as a clear oil with >98% purity (analytical HPLC). MS M+H= 737.7. The bis-hydrochloride salt was prepared by dissolving the oil in MeOH (3 mL), adding 4.0 N HCl in dioxane (20 mL, 5.0 equiv.). After stirring for 5 min., the solution was dripped into ether (1000 mL) with vigorous stirring in order to precipitate the product. Approximately 800 mL of the ether was decanted and the product was isolated from the remaining suspension by filtration using a Buchner funnel. The product was thoroughly rinsed with ether (300 mL), dried under vacuum, and dissolved in 20:80 acetonitrile:water (500 mL). The solution was frozen using a dry ice-acetone bath, and lyophilized to give compound 1 dihydrochloride salt as a white powder.

Example 2

Synthesis of 7-[(8-Methyl-3-(morpholin-4-ylcarbonylmethyl)-4(3H)-quinazolinon-2-yl) methyl]-16-[(S)-(2-methylphenylaminocarbonyl) prop-1-yl]-1,4,10,13-tetraoxa-7,16-diazacyclooctadecane (Compound 2 in Table I)

Using the above procedure of Example IA and substituting (S)-(+)-2-aminobutyric acid for (R)-(+)-2-aminobutyric acid, the title compound was prepared. MS M+H=737.7.

Example 3

Synthesis of

7-[(8-Methyl-3-(morpholin-4-ylcarbonylmethyl)-4(3H)-quinazolinon-2-yl)methyl]-16-[(2-methylphenylaminocarbonyl)prop-1-yl]-1,4,10,13-tetraoxa-7,16-diazacyclooctadecane (Compound 3 in Table I)

Figure 3:
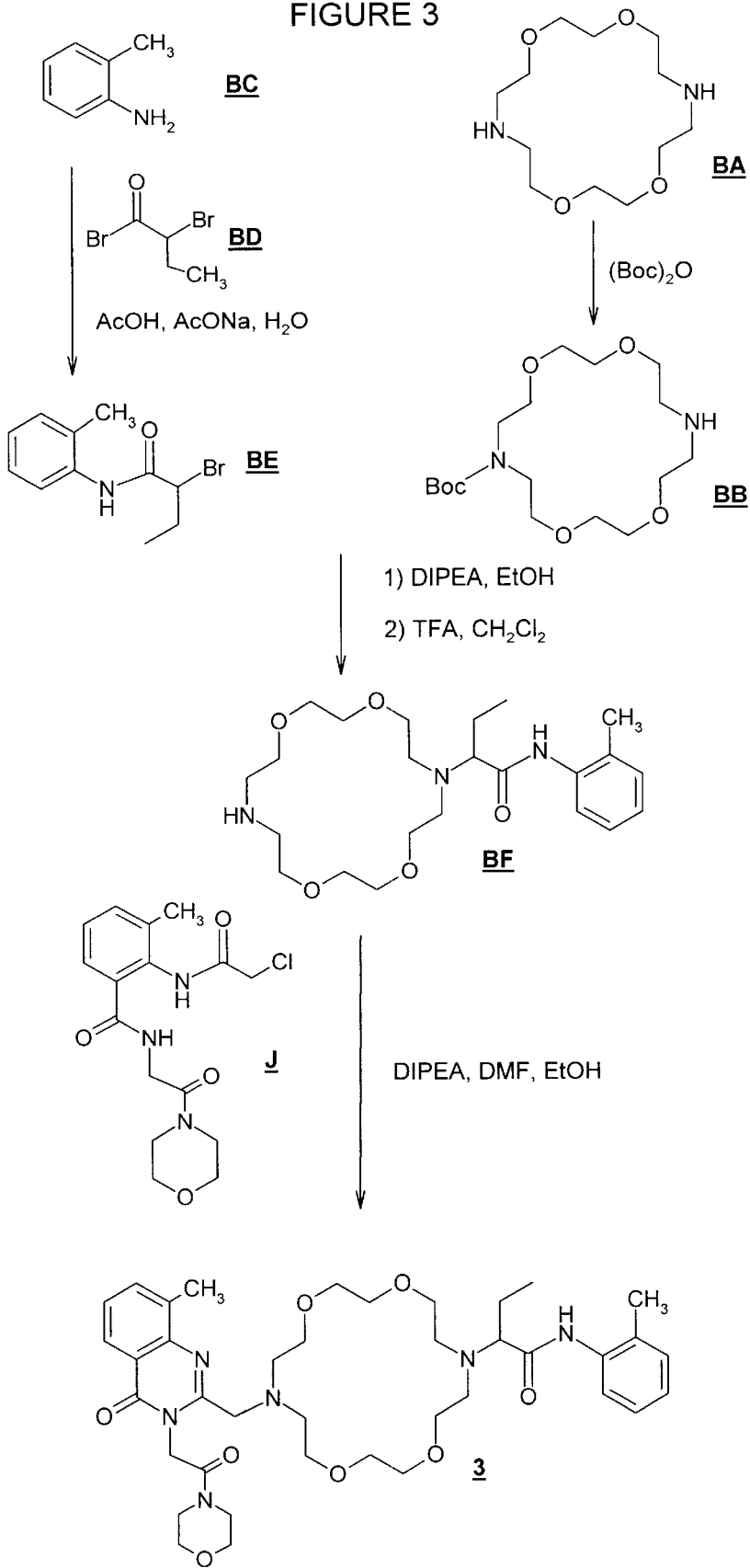
FIG. 3 illustrates another alternative synthesis of a representative compound of this invention using an intermediate of formula II.

This synthesis is illustrated in FIG. 3.

Step 1—Preparation of Compound BB

To a solution of 1,4,10,13-tetraoxa-7,16-diazacyclooctadecane BA (50.0 g, 0.19 mol) in 1,4-dioxane (700 mL) was added a solution of di-tert-butyl dicarbonate (41.5 g, 0.19 mol) in 1,4 dioxane (100 mL) over 1 h. After stirring overnight, dioxane was removed in vacuo and water (200 mL) was added to the remaining slurry with vigorous stirring. The white precipitate was removed by filtration (28 g of bis-Boc-18-crown-6) and the filtrate was lyophilized to dryness. Trituration of the solid with CH$_2$Cl$_2$ afforded compound BB (32 g, 46% yield) as a white solid.

Step 2—Preparation of Compound BE

α-Bromobutyryl bromide BD (80 mL, 0.66 mol) was added to a cooled mixture of o-toluidine BC (64 mL, 0.60 mol) and glacial acetic acid (520 mL) in a 2 L flask. The reaction mixture was stirred vigorously and a cold solution of sodium acetate trihydrate (204 g) in water (1100 mL) was added. A white precipitate began to form instantly. After 30 min., the solid was filtered off, washed with water and dried to give compound BE (200 g, 80%) as a white solid.

Step 3—Preparation of Compound BF

A solution of compound BE (10.5 g, 0.04 mol), N,N-diisopropylethylamine (7.0 mL, 0.04 mol) in ethanol (15 mL) was added to a 35 mL pressure tube containing N-Boc-1,4,10,13-tetraoxa-7,16-diazacyclooctadecane BB (7.5 g, 0.02 mol). The tube was closed and immersed into an oil bath maintained at 120° C. After 36 h, the reaction mixture was cooled and the organics were evaporated in vacuo. The oily residue was purified by elution through a plug of silica using 1% methanol/dichloromethane as the eluent. The organics were removed to give the desired product as well as unreacted compound BE. The crude product was dissolved in 50% trifluoroacetic acid/dichloromethane (50 mL). After stirring for 30 min. the reaction mixture was concentrated to a thick oil, redissolved in water (100 mL) and extracted with ethyl acetate (3×100 mL) to remove side products and residual compound BE. The aqueous solution was then basified to pH 10 with 1 N NaOH and the desired product was extracted with ethyl acetate (3×100 mL). The ethyl acetate layer was washed with brine, dried over anhydrous sodium sulfate, filtered and concentrated in vacuo to give compound BF (6.0 g, 66%) as a thick, light yellow oil. MS: M+H=438.

Step 4—Preparation of Compound 3

Compound J (8.9 g, 25.3 mmol, 1.3 equiv.), compound BF (8.5 g, 19.5 mmol, 1.0 equiv.), EtOH (15 mL), DMF (18 mL) and N, N-diisopropylethyl-amine (DIPEA) (5.1 mL, 29.2 mmol, 1.5 equiv.) were combined and then divided equally into three pressure tubes, each containing a magnetic stir bar. The tubes were sealed and heated to 120° C. with stirring. After 5 h, the contents of the tubes were combined in a separatory funnel and partitioned between 1 N HCl (200 mL) and EtOAc (500 mL). The aqueous layer was washed with EtOAc (4×400 mL). The acidic layer was made basic (pH>10) with the addition of 3 N NaOH (300 mL) and extracted with EtOAc (1×400 mL). The EtOAc layer was washed with saturated sodium bicarbonate (NaHCO$_3$) (250 mL) and saturated sodium chloride (NaCl) (200 mL). The solution was dried over anhydrous magnesium sulfate (MgSO$_4$) (50 g), filtered through filter paper using a Buchner funnel and the residue thoroughly rinsed with EtOAc (200 mL). The filtrate was concentrated to dryness on a rotary evaporator. The crude product was partially purified using a silica gel plug. A Buchner funnel was filled with a slurry of silica gel in CH$_2$Cl$_2$ (200 mL). A solution of impure product (15 g) in CH$_2$Cl$_2$ (10 mL) was loaded onto the plug and a vacuum was applied to draw the solution into the silica gel plug. The plug was eluted with $CH_2Cl_2$ (500 mL) using vacuum to pull solvent through the plug. The plug was eluted with 2:98 $MeOH:CH_2Cl_2$ (500 mL) and then eluted with 5:95 $MeOH:CH_2Cl_2$ (500 mL) until all product had eluted. The purified fractions were combined and concentrated to dryness on a rotary evaporator. This plug was used to remove all polar material before loading onto a preparatory HPLC. The resulting material was purified by HPLC as described in Example 1 to provide compound 3. MS M+H= 737.7.

Example 4

Synthesis of 7-[(8-Methyl-3-(morpholin-4-ylcarbonylmethyl)-4(3H)-quinazolinon-2-yl)methyl]-16-[1-(2,4,6-trimethylphenylaminocarbonyl)methyl]-1,4,10,13-tetraoxa-7,16-diazacyclooctadecane (Compound 4 in Table I)

Figure 4:
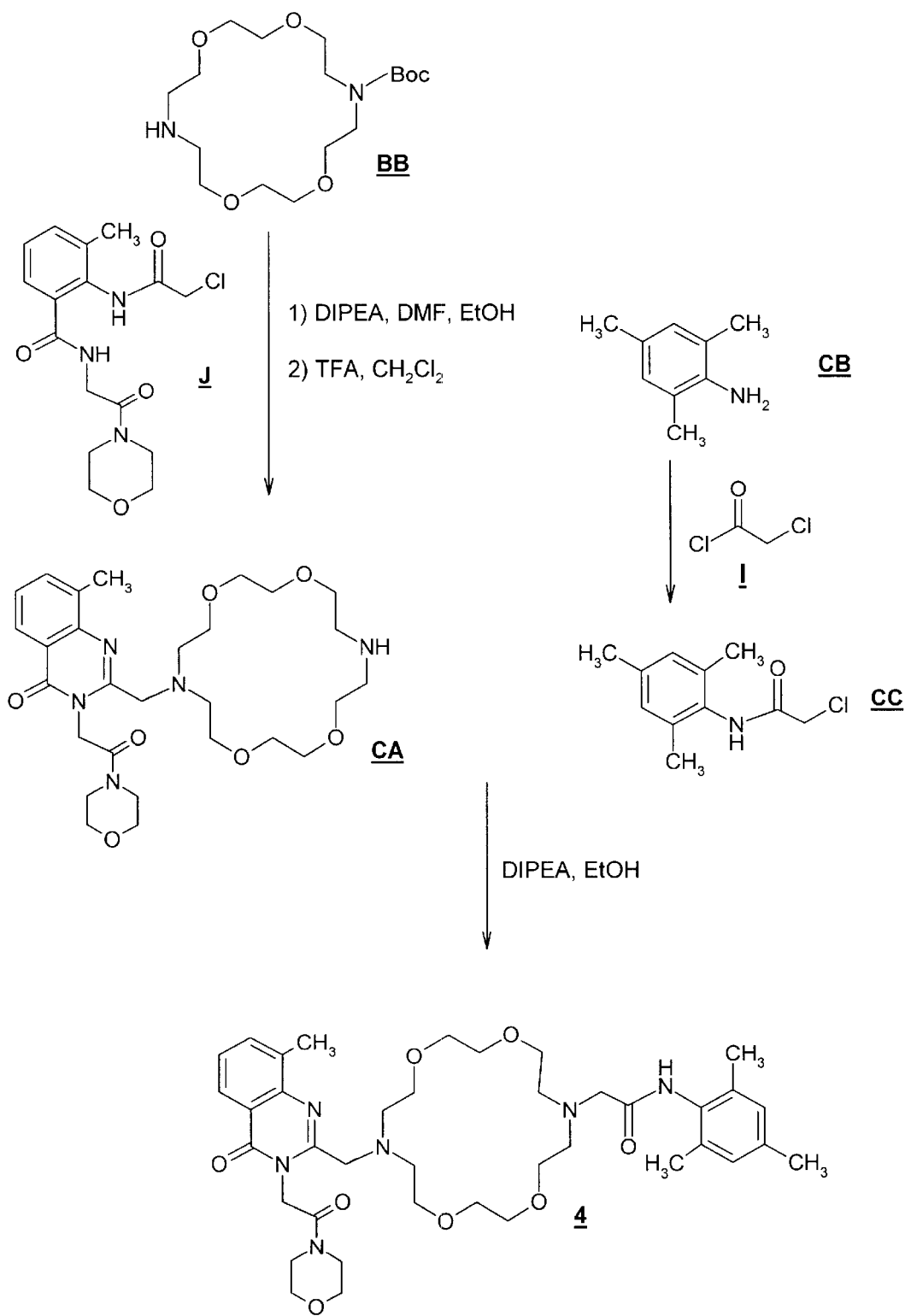
FIG. 4 illustrates the synthesis of a representative compound of this invention using an intermediate of formula III.

The following synthesis is illustrated in FIG. 4.
Step 1—Preparation of Compound CA A mixture of compound J (9.19 g, 26.0 mmol, 1.2 equiv.) and compound BB (7.84 g, 21.7 mmol, 1.0 equiv.) in EtOH (20 mL), DMF (10 mL) and N,N-diisopropylethylamine (DIPEA) (3.77 mL, 21.7 mmol, 1.0 equiv.) was heated to 95° C. for 12 h. The solvent was removed under reduced pressure and the residue re-dissolved in ethyl acetate (200 mL). The ethyl acetate layer was washed with brine, dried over magnesium sulfate, and concentrated to give an oil. The oil was re-dissolved in methylene chloride (50 mL) and loaded onto a pad of silica gel. The product was eluted with a gradient of 0 to 5% methanol in methylene chloride. The solvents were removed to give an oil which was dissolved in methylene chloride (30 mL) and cooled to 0° C. Trifluoroacetic acid (30 mL) was added and the solution was stirred for 4 h. The reaction mixture was concentrated to an oil which was re-dissolved in 1.0 N HCl (100 mL). The aqueous solution was washed with ethyl acetate (2×100 mL) and then made alkaline by dropwise addition of 6N NaOH until the pH was 12. The aqueous solution was then extracted with three 100 mL portions of ethyl acetate. The ethyl acetate extracts were combined, dried over magnesium sulfate and concentrated to give compound CA (9.36 g, 77%) as a pale brown oil with >90% purity.
Step 2—Preparation of Compound CC A solution of compound CB (13.5 g, 100 mmol, 1.0 equiv.) in acetic acid (88 mL) was cooled to 10° C. using a cold water bath. Chloroacetyl chloride I (10.7 mL, 120 mmol, 1.2 equiv.) was added all at once to the stirring reaction mixture. This was immediately followed by the addition of a solution of sodium acetate (34 g) in water (175 mL). The reaction mixture was warmed to room temperature while stirring for 20 min. Manual shaking was applied periodically to break up thick clumps of precipitate. The reaction mixture was filtered and the solid thoroughly rinsed with water (2 L). The solid was dried in to give compound CC (16.9 g, 79.7%) as a white solid.
Step 3—Preparation of Compound 4

A mixture of compound CA (0.34 g, 1.6 mmol, 1.8 equiv.), compound CC (0.5 g, 0.89 mmol, 1.0 equiv.), EtOH (1.5 mL), and N,N-diisopropylethylamine (DIPEA) (0.23 mL, 1.3 mmol, 1.5 equiv.) was taken in a pressure tube, containing a magnetic stir bar. The tube was sealed and heated to 100° C. with stirring for 5 h. The contents of the tube were placed in a separatory funnel and partitioned between 1 N HCl (20 mL) and EtOAc (50 mL). The aqueous layer was washed with EtOAc (4×40 mL). The acidic layer was made basic (pH>10) with the addition of 3 N NaOH (30 mL) and extracted with EtOAc (1×100 mL). The EtOAc layer was washed with saturated sodium bicarbonate ($NaHCO_3$) (50 mL) and saturated sodium chloride (NaCl) (20 mL). The solution was dried over anhydrous magnesium sulfate ($MgSO_4$) (10 g), filtered, and the residue was thoroughly rinsed with EtOAc (50 mL). The filtrate was concentrated to dryness and the crude product was purified using a silica gel column using 2:98 $MeOH:CH_2Cl_2$ (500 mL) and then eluted with 5:95 $MeOH:CH_2Cl_2$ (500 mL) as the eluent. The purified fractions were combined and concentrated to dryness to the free amine as an oil. MS M+H=737.3. The bis-hydrochloride salt was prepared by dissolving the oil in MeOH (1 mL) and adding 4.0 N HCl in dioxane (1.1 mL, 5.0 equiv.) and stirring for 5 min. This solution was dripped into ether (100 mL) with vigorous stirring in order to precipitate the product. The product was filtered, thoroughly rinsed with ether (30 mL), dried under vacuum, and dissolved in 20:80 acetonitrile:water (50 mL). The solution was frozen using a dry ice-acetone bath, and lyophilized to yield compound 4 as a white powder.

Using the above procedures and the appropriate starting materials, the following compounds were prepared:

Example 5

7-[(8-Methyl-3-(morpholin-4-ylcarbonylmethyl)-4(3H)-quinazolinon-2-yl)methyl]-16-[1-(2-methylphenylaminocarbonyl)ethyl]-1,4,10,13-tetraoxa-7,16-diazacyclooctadecane (Compound 5) (Prepared according to the procedure of Example 3) MS M+H=723.5.

Example 6

7-[(8-Methyl-3-(morpholin-4-ylcarbonylmethyl)-4(3H)-quinazolinon-2-yl)methyl]-16-[(2,6-dimethylphenylaminocarbonyl)prop-1-yl]-1,4,10,13-tetraoxa-7,16-diazacyclooctadecane (Compound 6) (Prepared according to the procedure of Example 3) MS M+H=751.4.

Example 7

7-[(8-Methyl-3-(morpholin-4-ylcarbonylmethyl)-4(3H)-quinazolinon-2-yl)methyl]-16-[(2-ethylphenylaminocarbonyl)prop-1-yl]-1,4,10,13-tetraoxa-7,16-diazacyclooctadecane (Compound 7) (Prepared according to the procedure of Example 3)MS M+H=751.4.

Example 8

7-[(8-Methyl-3-(morpholin-4-ylcarbonylmethyl)-4(3H)-quinazolinon-2-yl)methyl]-16-[(2-methylphenylaminocarbonyl)but-1-yl]-1,4,10,13-tetraoxa-7,16-diazacyclooctadecane (Compound 8) (Prepared according to the procedure of Example 3) MS M+H=751.5.

Example 9

7-[(8-Methyl-3-(morpholin-4-ylcarbonylmethyl)-4(3H)-quinazolinon-2-yl)methyl]-16-[(2,6-dimethylphenylaminocarbonyl)methyl)]-1,4,10,13-tetraoxa-7,16-diazacyclooctadecane (Compound 9) (Prepared according to the procedure of Example 3) MS M+H =723.5.

Example 10

7-[(8-Methyl-3-(morpholin-4-ylcarbonylmethyl)-4(3H)-quinazolinon-2-yl)methyl]-16-[(2-isopropylphenylaminocarbonyl)methyl]-1,4,10,13-tetraoxa-7,16-diazacyclooctadecane (Compound 10) (Prepared according to the procedure of Example 4) MS M+H=737.3.

Example 11
7-[(8-Methyl-3-(morpholin-4-ylcarbonylmethyl)-4 (3H)-quinazolinon-2-yl)methyl]-16-[(2-ethylphenylaminocarbonyl)methyl]-1,4,10,13-tetraoxa-7,16-diazacyclooctadecane (Compound 11) (Prepared according to the procedure of Example 4) MS M+H=723.5.

Example 12
7-[(8-Methyl-3-(morpholin-4-ylcarbonylmethyl)-4 (3H)-quinazolinon-2-yl)methyl]-16-[(2-methylphenylaminocarbonyl)methyl]-1,4,10,13-tetraoxa-7,16-diazacyclooctadecane (Compound 12) (Prepared according to the procedure of Example 4) MS M+H=709.4.

Example 13
7-[(8-Methyl-3-(morpholin-4-ylcarbonylmethyl)-4 (3H)-quinazolinon-2-yl)methyl]-16-[(2-ethyl-6-methylphenylaminocarbonyl)methyl]-1,4,10,13-tetraoxa-7,16-diazacyclooctadecane (Compound 13) (Prepared according to the procedure of Example 4) MS M+H=737.3.

Example 14
7-[(8-Methyl-3-(morpholin-4-ylcarbonylmethyl)-4 (3H)-quinazolinon-2-yl)prop-1-yl]-16-[(2-methylphenylaminocarbonyl)prop-1-yl]-1,4,10,13-tetraoxa-7,16-diazacyclooctadecane (Compound 14) (Prepared according to the procedure of Example 3 except after Step 4, the resulting intermediate was heated in acetic acid/ethanol to form quinazolinone ring) MS M+H=765.3.

Example 15
7-[(8-Methyl-3-(morpholin-4-ylcarbonylmethyl)-4 (3H)-quinazolinon-2-yl)methyl]-16-[(2,3-dimethylphenylaminocarbonyl)methyl]-1,4,10,13-tetraoxa-7,16-diazacyclooctadecane (Compound 15) (Prepared according to the procedure of Example 4) MS M+H=723.4.

Example 16
7-[(8-Methyl-3-(morpholin-4-ylcarbonylmethyl)-4 (3H)-quinazolinon-2-yl)methyl]-16-[(2,4-dimethylphenylaminocarbonyl)methyl]-1,4,10,13-tetraoxa-7,16-diazacyclooctadecane (Compound 16) (Prepared according to the procedure of Example 4) MS M+H=723.4.

Example 17
7-[(8-Methyl-3-(morpholin-4-ylcarbonylmethyl)-4 (3H)-quinazolinon-2-yl)methyl]-16-[(2,5-dimethylphenylaminocarbonyl)methyl]-1,4,10,13-tetraoxa-7,16-diazacyclooctadecane (Compound 17) (Prepared according to the procedure of Example 4) MS M+H=723.4.

Example 18
7-[(8-Methyl-3-(morpholin-4-ylcarbonylmethyl)-4 (3H)-quinazolinon-2-yl)methyl]-16-[(3,4-dimethylphenylaminocarbonyl)methyl]-1,4,10,13-tetraoxa-7,16-diazacyclooctadecane (Compound 18) (Prepared according to the procedure of Example 4) MS M+H=723.4.

Example 19
7-[(8-Methyl-3-(morpholin-4-ylcarbonylmethyl)-4 (3H)-quinazolinon-2-yl)methyl]-16-[(3,5-dimethylphenylaminocarbonyl)methyl]-1,4,10,13-tetraoxa-7,16-diazacyclooctadecane (Compound 19) (Prepared according to the procedure of Example 4) MS M+H=723.2.

Example 20
7-[(3-(Morpholin-4-ylcarbonylmethyl)-4(3H)-quinazolinon-2-yl)methyl]-16-[(2-methylphenylaminocarbonyl)methyl]-1,4,10,13-tetraoxa-7,16-diazacyclooctadecane (Compound 20) (Prepared according to the procedure of Example 3) MS M+H=723.6.

Example 21

Preparation of Injectable Formulation

The dihydrochloride salt of Compound 1 (2.2 grams) was dissolved in 50 mL of water. The pH was adjusted to 4.75 by slow addition of 0.1 M NaOH with very efficient stirring (pH adjustment may require up to 4 hours, since during the addition of 0.1 M NaOH, compound 1 precipitates heavily and re-dissolves very slowly.) About 17–18 mLs of 0.1M NaOH are needed for the pH adjustment. Mannitol (1.57 grams) and sucrose (3.71 grams) were then dissolved in the above solution. The volume was adjusted to 95 mL with water and the pH was adjusted with 0.1 M NaOH and/or 0.1 M HCl to 4.7–4.8, if necessary. The volume was then adjusted to 100 mL with water and the formulation was sterile filtered under aseptic conditions.

Biological Assay Procedures:

The following procedures were used to assay the biological properties of the compounds of formula I.

Example 22

Whole-Cell Voltage Clamp

The whole cell variant of the patch-clamp method (Hamill et al., *Pflügers Arch.* 391:85–100, 1981) was used to measure $Na^+$ currents in $GH_3$ cells. The external solution contained (in mmol) 150 choline Cl, 0.2 $CdCl_2$, 2 $CaCl_2$, and 10 hydroxethylpiperazine ethane sulfonic acid (HEPES) adjusted to pH 7.4 with tetramethyl hydroxide. Micropipettes were fabricated and had a tip resistance of ~1 MΩ when filled with an $Na^+$ solution containing (in mmol) 100 NaF, 30 NaCl, 10 EGTA (ethylene glycol-bis(O-aminoethyl ether)-N,N,N',N'-tetraacetic acid), and 10 hydroxyethylpiperazineethane sulfonic acid, adjusted to pH 7.2 with CsOH.

The junction potential of electrodes was nulled before seal formation. After the rupture of the patch membrane, the cell was allowed to equilibrate with the pipette solution for at least 15 min at the holding potential of –100 mV. Under these reversed $Na^+$ gradient conditions, outward $Na^+$ currents were activated at approximately –30 mV. Test compounds, at appropriate concentrations, were applied to cells with a flow rate of about 0.12 mL/min via a series of narrow-bored capillary tubes positioned within 200 μm of the cell. Typically, the more soluble salt form, rather than the free base, was used. Washout of drugs was performed via a tube containing the external solution without drug present. Voltage-clamp protocols were created with pClamp software (Axon Instruments, Inc., Foster City, Calif.). Leak and capacitance were subtracted by a leak and capacity compensator (Hille and Campbell, *J. Gen. Physiol.* 67:265–93, 1976). Additional compensation was achieved by the patch clamp device (EPC7, List-Electronic, Darmstadt/Eberstadt, Germany). All experiments were performed at room temperature. At the end of the experiments, the drift in the junction potential was generally <2 mV.

Example 23

Rat Sciatic Nerve Sucrose-Gap Assay

Sprague-Dawley rats (42–56 days old) obtained from Charles River Laboratories were used in these experiments. Animals were euthanized and the sciatic nerves were excised and maintained in Ringer solution.

The Ringer solution contained: 124 mM NaCl, 3 mM KCl, 1.3 mM $NaH_2PO_4$, 2 mM $MgCl_2.H_2O$, 2 mM $MgCl_2$-

$6H_2O$, 26 mM $NaHCO_3$, and 10 mM Dextrose. The pH was adjusted to 7–7.5 using bubbled 95% $O_2$-5% $CO_2$ This Ringer solution was used for storing nerves and for filling the two stimulating pools (500 uL) and the recording "intracellular" pool.

The compounds to be tested for local anesthetic activity were prepared as 10 mM solutions in 15% PEG 400. The solutions were stored at 4° C. to minimize loss of potency. The working solutions were prepared by diluting stock solution in Ringer solution just prior to their use in experiments.

Segments of nerves measuring 5 mm were desheathed and mounted in a polycarbonate sucrose-gap chamber. In the chamber, the nerves were laid across a series of pools and within a cylindrical gap with the proximal end in the "test" pool. Petroleum jelly (Vaseline, Cheeseborough Pons) was used to create watertight seals around regions of the nerves passing between aqueous pools.

The proximal end of the nerve was stimulated by a pair of bipolar Ag/AgCl electrodes inserted into the stimulating pools. The "test" pool (500 $\mu$L volume) contained the Ag/AgCl electrode that recorded the extracellular electrical potential. Flowing at 1.0 mL/min, a nonionic sucrose solution (320 mM) prevented the action potential from propagating beyond the test pool. The intracellular potential, conducted passively through the sucrose gap to the distal end of the preparation, was recorded using Ag/AgCl ("intracellular") electrodes in a Ringers containing pool. Using a stimulator (A360 Stimulus Isolator, WPI), nerves were stimulated for 0.1 ms at two times the intensity required to induce the maximal compound action potential (CAP). The electrical signal from the nerve, the compound action potential (CAP) from large myelinated fibres, was amplified 10 times using an amplifier (IsoDam 8, WPI). The signal was displayed on an oscilloscope and also recorded on a computer using BioPak software. A nerve preparation was considered acceptable if the CAP measured not less than 10 mV, and the experiment was carried out after CAP stabilized (i.e. did not vary more than 1–2 mV over a 10–20 min period).

Nerves were stimulated at less than 1 Hz during the full experiment time to assess "tonic" block, and "phasic" block was measured by 50 Hz trains applied 400 ms every 4 secs. All data were recorded at room temperature.

Example 24

Measurement of Sciatic Nerve Block in the Rat

Sprague-Dawley male rats in groups of 3–6 were injected percutaneously with a 27 G needle close to the sciatic nerve (about one third of the distance between the greater trochanter and the ischial tuberosity and caudal to the greater trochanter) with 0.2 mL of 10–90 mM solution of test compounds, pH 3–4.5 (i.e., compounds of Formula I, lidocaine and bupivacaine (Marcaine®)). Animals were observed at least three times on the day of the procedure, and each day thereafter.

At 3, 15 and 30 minutes and every 30 minutes thereafter for up to 10 hours after injection, the animals were assessed for motor and sensory nerve block. Where the anesthesia lasted longer than 10 hours, daily assessments were made for up to 5 days. Motor deficit was assessed by placing the animal on a flat surface and noting whether the paw was spread out under the animal (normal position) or whether it was kept closed and not used for locomotion (deficit). For assessment of sensory block, the animal was held above the bench surface and the skin between the two lateral-most toes was pinched using a pair of "rat-tooth forcepts". A withdrawal response is normal, whereas no response indicates sensory block.

In animals that showed full recovery of motor and sensory nerve function within 48 hours, a second compound was tested after a period of one week has elapsed. The tests are performed in the same way as described above, but on the contralateral limb. Results are analyzed for statistical significance using a one way analysis of variance.

Example 25

Surgical Anesthesia and/or Post-operative Analgesia Procedures

Compounds of formula I are used in patients requiring both surgical anesthesia and post-operative analgesia (e.g., surgical repair of an inguinal hernia) or post-procedure pain relief only (e.g., post-operative pain relief of long duration; post-arthroscopy).

A patient requiring surgical repair of an inguinal hernia is prepared for surgery. It is desired to provide local anesthesia prior to incision, and for 18 to 36 hours post-operatively. Accordingly, prior to incision, a sterile injectable solution containing about 0.1–2.5% of a compound of formula I (with or without 5 $\mu$g/mL epinephrine, at the discretion of the surgeon) is infiltrated incrementally at the site of incision until the patient no longer senses cutaneous pain when pinched with a hemostat. Additional drug is administered during the procedure if required. The total volume of solution required is in the range of about 10–30 mL.

For post-operative analgesia in a patient requiring a major abdominal operation (e.g., a C-section), who will receive a general anesthetic during the operation, the wound area is infiltrated either pre-incisionally or at the end of the procedure with a compound of formula I.

For relief of joint pain following an arthroscopic procedure, the patient's joint is infiltrated with a compound of formula I.

The compounds of this invention were found to exhibit significant activity in the assays described above, thus demonstrating their utility as local anesthetics and as modulators of sodium channel activity.

While the present invention has been described with reference to specific embodiments thereof, it should be understood by those skilled in the art that various changes may be made and equivalents may be substituted without departing from the true spirit and scope of the invention. In addition, many modifications may be made to adapt a particular situtation, material, composition of matter, process, process step or steps, to the objective, spirit and scope of the present invention. All such modifications are intended to be within the scope of the claims appended hereto. Additionally, all publications, patents, and patent documents cited herein are incorporated by reference herein in their entirety to the same extent as if they had been individually incorporated by reference.

What is claimed is:
1. A compound of formula I:

wherein
- R¹ is selected from the group consisting of hydrogen, $C_{1-6}$ alkyl and $C_{1-6}$ alkoxy;
- R² is selected from the group consisting of hydrogen, $C_{1-6}$ alkyl and $C_{1-6}$ alkoxy;
- R³ is hydrogen or $C_{1-6}$ alkyl;
- R⁴ is hydrogen or $C_{1-6}$ alkyl;
- R⁵ is hydrogen or $C_{1-6}$ alkyl;
- each R⁶ is independently selected from the group consisting of $C_{1-6}$ alkyl and $C_{1-6}$ alkoxy;
- n is an integer from 0 to 3;
- or pharmaceutically acceptable salts or stereoisomers thereof.

2. The compound of claim 1, wherein R¹ is $C_{1-4}$ alkyl.
3. The compound of claim 2, wherein R¹ is methyl.
4. The compound of claim 1, wherein R² is hydrogen.
5. The compound of claim 1, wherein R³ is hydrogen, methyl or ethyl.
6. The compound of claim 1, wherein R⁴ is hydrogen or $C_{1-4}$ alkyl.
7. The compound of claim 6, wherein R⁴ is hydrogen, methyl or ethyl.
8. The compound of claim 1, wherein R⁵ is hydrogen.
9. The compound of claim 1, wherein each R⁶ is independently $C_{1-4}$ alkyl.
10. The compound of claim 9, wherein each R⁶, and the phenyl ring to which they are attached, form a 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6,-trimethylphenyl, 2,4,5-trimethylphenyl, 2,4,6-trimethylphenyl, 3,4,5-trimethylphenyl group, 2-ethylphenyl, 2-ethyl-6-methylphenyl or 2-isopropylphenyl group.
11. The compound of claim 1, wherein R¹ is $C_{1-4}$ alkyl; R², R³ and R⁵ are hydrogen; R⁴ is hydrogen or $C_{1-4}$ alkyl; R⁶ is $C_{1-4}$ alkyl; and n is an integer from 1 to 3.
12. The compound of claim 1, wherein R¹ is methyl; R², R³ and R⁵ are hydrogen; R⁴ is hydrogen, methyl or ethyl; R⁶ is methyl; and n is an integer from 1 to 3.
13. A compound selected from the group consisting of:
  7-[(8-methyl-3-(morpholin-4-ylcarbonylmethyl)-4(3H)-quinazolinon-2-yl)methyl]-16-[(R)-(2-methylphenylaminocarbonyl)prop-1-yl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(S)-(2-methylphenylaminocarbonyl)prop-1-yl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2-methylphenylaminocarbonyl)prop-1-yl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2,4,6-trimethylphenylaminocarbonyl)methyl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[1-(2-methylphenylaminocarbonyl)ethyl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2,6-dimethylphenylaminocarbonyl)prop-1-yl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2-ethylphenylaminocarbonyl)prop-1-yl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2-methylphenylaminocarbonyl)but-1-yl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2,6-dimethylphenylaminocarbonyl)methyl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2-isopropylphenylaminocarbonyl)methyl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2-ethylphenylaminocarbonyl)methyl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2-methylphenylaminocarbonyl)methyl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2-ethyl-6-methylphenylaminocarbonyl)methyl]-1,4,10,13-tetraoxa-7,16-diazacyclooctadecane;
  7-[(8-methyl-3-(morpholin-4-ylcarbonylmethyl)-4(3H)-quinazolinon-2-yl)prop-1-yl]-16-[(2-methylphenylaminocarbonyl)prop-1-yl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2,3-dimethylphenylaminocarbonyl)methyl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2,4-dimethylphenylaminocarbonyl)methyl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(2,5-dimethylphenylaminocarbonyl)methyl]-1,4,10,13-tetraoxa-7,16-diazacyclooctadecane;
  7-[(8-methyl-3-(morpholin-4-ylcarbonylmethyl)-4(3H)-quinazolinon-2-yl)methyl]-16-[(3,4- dimethylphenylaminocarbonyl)methyl]-1,4,10,13-tetraoxa-7,16-diazacyclooctadecane;

7-[(8-methyl-3-(morpholin-4-ylcarbonylmethyl)-4(3H)-quinazolinon-2-yl)methyl]-16-[(3,5-dimethylphenylaminocarbonyl)methyl]-1,4,10,13-tetraoxa-7,16-diazacyclooctadecane;

7-[(3-(morpholin-4-ylcarbonylmethyl)-4(3H)-quinazolinon-2-yl)methyl]-16-[(2-methylphenylaminocarbonyl)methyl]-1,4,10,13-tetraoxa-7,16-diazacyclooctadecane;

or pharmaceutically acceptable salts thereof.

14. 7-[(8-Methyl-3-(morpholin-4-ylcarbonylmethyl)-4(3H)-quinazolinon-2-yl)methyl]-16-[(R)-(2-methylphenylaminocarbonyl)prop-1-yl]-1,4,10,13-tetraoxa-7,16-diazacyclooctadecane, or a pharmaceutically acceptable salt thereof.

15. 7-[(8-Methyl-3-(morpholin-4-ylcarbonylmethyl)-4(3H)-quinazolinon-2-yl)methyl]-16-[(S)-(2-methylphenylaminocarbonyl)prop-1-yl]-1,4,10,13-tetraoxa-7,16-diazacyclooctadecane, or a pharmaceutically acceptable salt thereof.

16. A compound of formula II:

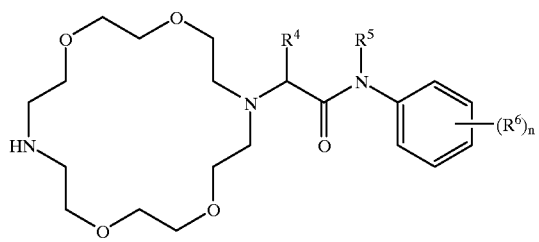

II wherein $R^4$ is hydrogen or $C_{1-6}$ alkyl;

$R^5$ is hydrogen or $C_{1-6}$ alkyl;

each $R^6$ is independently selected from the group consisting of $C_{1-6}$ alkyl and $C_{1-6}$ alkoxy;

n is an integer from 0 to 3;

or salts or stereoisomers thereof.

17. The compound of claim 1, wherein $R^1$ is hydrogen; $R^4$ is hydrogen or $C_{1-4}$ alkyl; $R^6$ is $C_{1-4}$ alkyl; and n is an integer from 1 to 3.

18. A compound of formula III:

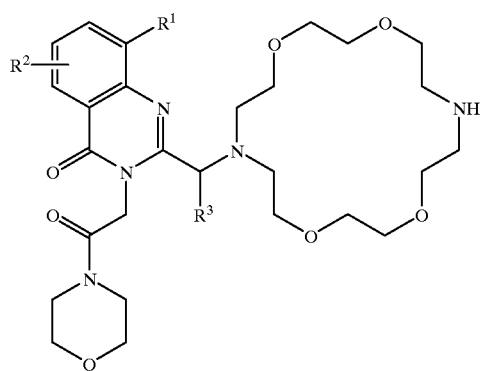

III wherein $R^1$ is selected from the group consisting of hydrogen, $C_{1-6}$ alkyl and $C_{1-6}$ alkoxy;

$R^2$ is selected from the group consisting of hydrogen, $C_{1-6}$ alkyl and $C_{1-6}$ alkoxy;

$R^3$ is hydrogen or $C_{1-6}$ alkyl;

or salts or stereoisomers thereof.

19. The compound of claim 18, wherein $R^1$ is $C_{1-4}$ alkyl; and $R^2$ and $R^3$ are hydrogen.

20. A pharmaceutical composition comprising a pharmaceutically acceptable carrier and a therapeutically effective amount of a compound of any of claims 1–15.

21. The pharmaceutical composition of claim 20, wherein the pharmaceutical composition further comprises a therapeutically effective amount of lidocaine.

22. A method for producing local anesthesia or analgesia in a mammal, the method comprising administering to a mammal a pharmaceutical composition comprising a pharmaceutically acceptable carrier and a therapeutically effective amount of a compound of any of claims 1–15.

23. A method for treating a disease or medical condition associated with or modulated by a voltage-gated sodium channel, the method comprising administering to a patient in need of treatment a pharmaceutical composition comprising a pharmaceutically acceptable carrier and a therapeutically effective amount of a compound of any of claims 1–15, wherein said disease or medical condition is selected from the group consisting of: pain; depression; seizures; stroke; ischemia; asthma; rapid heartbeat; cardiac arrhythmia; natriuresis; proctitis; active distal ulcerative colitis; inflammatory bowel disease; and irritable bowel syndrome.

24. A process for preparing a compound of formula I:

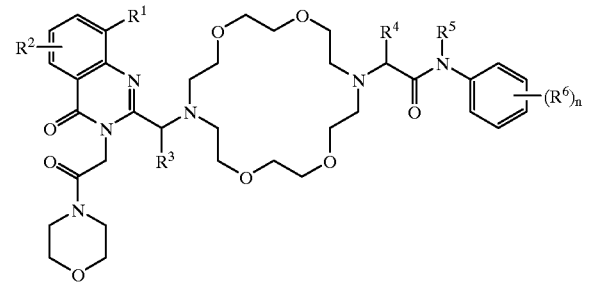

I wherein $R^1$ is selected from the group consisting of hydrogen, $C_{1-6}$ alkyl and $C_{1-6}$ alkoxy;

$R^2$ is selected from the group consisting of hydrogen, $C_{1-6}$ alkyl and $C_{1-6}$ alkoxy;

$R^3$ is hydrogen or $C_{1-6}$ alkyl;

$R^4$ is hydrogen or $C_{1-6}$ alkyl;

$R^5$ is hydrogen or $C_{1-6}$ alkyl;

each $R^6$ is independently selected from the group consisting of $C_{1-6}$ alkyl and $C_{1-6}$ alkoxy;

n is an integer from 0 to 3; the process comprising contacting a compound of formula II:

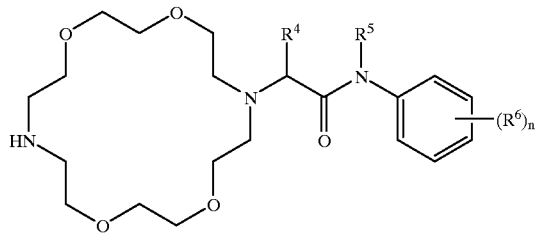

with a compound of formula IV:

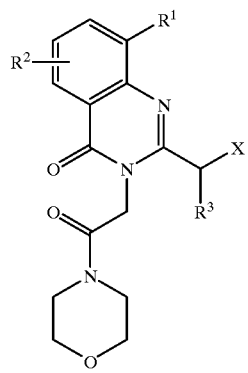

wherein X is a leaving group; to provide a compound of formula I.

25. A process for preparing a compound of formula I:

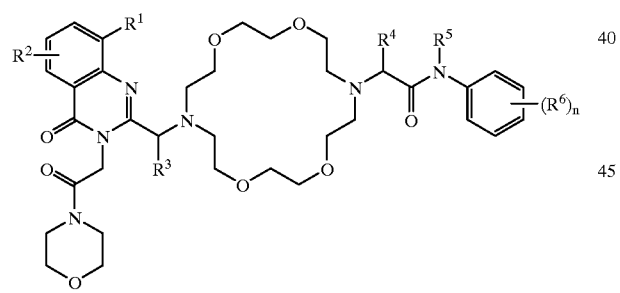

wherein

R$^1$ is selected from the group consisting of hydrogen, C$_{1-6}$ alkyl and C$_{1-6}$ alkoxy;

R$^2$ is selected from the group consisting of hydrogen, C$_{1-6}$ alkyl and C$_{1-6}$ alkoxy;

R$^3$ is hydrogen or C$_{1-6}$ alkyl;

R$^4$ is hydrogen or C$_{1-6}$ alkyl;

R$^5$ is hydrogen or C$_{1-6}$ alkyl;

each R$^6$ is independently selected from the group consisting of C$_{1-6}$ alkyl and C$_{1-6}$ alkoxy;

n is an integer from 0 to 3; the process comprising contacting a compound of formula III:

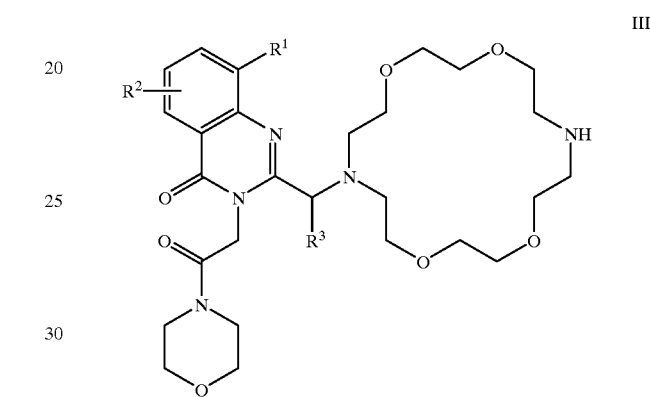

with a compound of formula V:

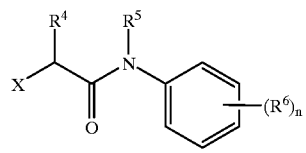

wherein X is a leaving group; to provide a compound of formula I.

* * * * *

UNITED STATES PATENT AND TRADEMARK OFFICE
CERTIFICATE OF CORRECTION

PATENT NO.   : 6,355,637 B1
DATED        : March 12, 2002
INVENTOR(S)  : Axt et al.

It is certified that error appears in the above-identified patent and that said Letters Patent is hereby corrected as shown below:

Column 39,
Line 43, please replace "$R^1$" with -- $R^5$ --.

Column 40,
Lines 9 and 18, at each occurrence, please replace "phara-" with -- phar --.

Signed and Sealed this

Thirteenth Day of September, 2005

JON W. DUDAS
*Director of the United States Patent and Trademark Office*